(12) United States Patent
Kanzaki et al.

(10) Patent No.: US 8,314,835 B2
(45) Date of Patent: Nov. 20, 2012

(54) ENDOSCOPE ADAPTER INCLUDING LIGHT EMITTING DIODE, AND ADAPTER TYPE ENDOSCOPE

(75) Inventors: Kazuhiro Kanzaki, Hachioji (JP); Junki Ishibashi, Hachioji (JP); Kenichi Zen, Tachikawa (JP)

(73) Assignee: Olympus Corporation (JP)

( * ) Notice: Subject to any disclaimer, the term of this patent is extended or adjusted under 35 U.S.C. 154(b) by 557 days.

(21) Appl. No.: 12/358,493

(22) Filed: Jan. 23, 2009

(65) Prior Publication Data

US 2010/0188493 A1 Jul. 29, 2010

(51) Int. Cl.
*H04N 7/18* (2006.01)
(52) U.S. Cl. ............... 348/75; 348/62; 348/63; 348/69; 348/76; 348/362; 348/363
(58) Field of Classification Search .................. 348/62, 348/63, 69, 75, 76, 362, 363
See application file for complete search history.

(56) References Cited

U.S. PATENT DOCUMENTS

| | | | | |
|---|---|---|---|---|
| 5,876,427 | A * | 3/1999 | Chen et al. | 607/88 |
| 7,959,339 | B2 * | 6/2011 | Watanabe | 362/574 |
| 2006/0183977 | A1 * | 8/2006 | Ishigami et al. | 600/179 |
| 2007/0100202 | A1 * | 5/2007 | Murata | 600/109 |
| 2008/0275302 | A1 * | 11/2008 | Hosaka | 600/139 |

FOREIGN PATENT DOCUMENTS

| | | |
|---|---|---|
| JP | 58-36726 | 3/1983 |
| JP | 60-203230 | 10/1985 |
| JP | 10-229966 | 9/1998 |
| JP | 10-328131 | 12/1998 |
| JP | 2004-313241 | 11/2004 |
| JP | 2005-027851 | 2/2005 |
| JP | 2005-110879 | 4/2005 |
| JP | 2006-106166 | 4/2006 |
| JP | 2006-333945 | 12/2006 |
| JP | 2007-312809 | 12/2007 |

OTHER PUBLICATIONS

Office Action issued by the Japanese Patent Office on Nov. 8, 2011 in connection with corresponding Japanese Patent Application No. 2006-212558.

* cited by examiner

*Primary Examiner* — Rupal Dharia
*Assistant Examiner* — Van Kim T Nguyen
(74) *Attorney, Agent, or Firm* — Ostrolenk Faber LLP

(57) ABSTRACT

An endoscope adapter including a light emitting diode includes: a detachable portion to be attached to an adapter attaching portion provided on a distal end portion of an insertion portion, the insertion portion including inside thereof at least one image-forming optical system; an adapter main body including an adapter side observation optical system whose optical axis is coincident with an optical axis of the image-forming optical system; a contact pin which enables power supply to the light emitting diode to be turned on when the detachable portion is attached to the adapter attaching portion; and a resistor arranged in a space formed in the endoscope adapter to determine a type of the endoscope adapter.

13 Claims, 21 Drawing Sheets

ENDOSCOPE ADAPTER INCLUDING LIGHT EMITTING DIODE, AND ADAPTER TYPE ENDOSCOPE

BACKGROUND OF THE INVENTION

1. Field of the Invention

The present invention relates to an endoscope adapter including a light emitting diode, and to an adapter type endoscope configured by connecting the endoscope adapter.

2. Description of the Related Art

Conventionally, endoscope apparatuses have been widely used in medical fields and industrial fields. The observation object of the endoscope is the inside of a living body, a pipe, and the like. Therefore, when an endoscopic examination is performed, a light source for illuminating the observation object is needed. In a common endoscope apparatus, a light source apparatus which supplies illumination light is prepared as an external apparatus of the endoscope. The illumination light emitted by the light source apparatus is supplied to a light guide provided in an insertion portion of the endoscope, and is transmitted to the distal end portion of the insertion portion via the light guide. Then, the illumination light is emitted towards the observation object from an illumination window arranged at the insertion portion distal end portion.

In recent years, there is proposed an endoscope which, instead of transmitting the illumination light emitted by the light source apparatus to the distal end portion of the insertion portion via the light guide, is configured to have a light emitting device such as a light emitting diode (hereinafter abbreviated as LED) provided at the distal end portion of the insertion portion, and to illuminate the observation object with the light emitted by the light emitting device. In the case where the endoscope having the light emitting device provided at the distal end portion, is configured such that an image of the observation object illuminated by the light emitting device is picked up by an image pickup device, an electrical cable extended from the image pickup device, and an electrical cable for supplying electric power to the light emitting device are inserted in the insertion portion. This makes it possible to realize an endoscope having a small diameter and a simple configuration, and having a high performance.

However, for an endoscope apparatus, a plurality of types of adapters are prepared and there is a case where the number of LEDs to be provided is different depending on the types of the adapters. The plurality of types of adapters are selectively and exchangeably attachable to an insertion portion. In such an endoscope apparatus, required amount of electric power is different depending on the number of LEDs to be provided to each of the adapters. Therefore, if appropriate amount of electric power can not be supplied to the LEDs depending on the adapter to be attached, appropriate amount of light required for illumination might not be obtained.

In order to eliminate the defect, Japanese Patent Application Laid-Open Publication No. 2006-333945, for example, discloses an endoscope apparatus capable of easily obtaining appropriate amount of illumination light depending on a type of adapter to be attached, with a simple configuration. In the endoscope apparatus, when an adapter is attached to an insertion portion, for example, a power supply portion and an illumination portion are electrically connected and the type of adapter is determined using a resistor provided to the adapter. Based on the determination result, the amount of the electric power supplied from the power supply portion is corrected and the corrected amount of electric power is supplied to LEDs.

In recent years, the adapters for endoscope apparatus include a direct view type and a side view type, and in addition, a plurality of types of adapters such as a monocular type, a stereo type and the like are prepared according to intended purposes, for the direct view type and the side view type, respectively. Some endoscope apparatus adapters are provided with various types of sensors including a temperature sensor. With a reduction in diameter of insertion portions of endoscopes, these adapters are reduced in size. With the reduction in size of the adapters, a space on an end surface of a connecting portion between the adapter and the insertion portion is reduced. This makes it difficult to arrange electric elements such as a resistor for determining the type of the adapter on the end surface on the adapter side.

SUMMARY OF THE INVENTION

An endoscope adapter including a light emitting diode according to the present invention includes: a detachable portion to be attached to an adapter attaching portion provided on a distal end portion of an insertion portion, the insertion portion including inside thereof at least one image-forming optical system; an adapter main body including an adapter side observation optical system whose optical axis is coincident with an optical axis of the image-forming optical system; a contact pin which enables power supply to the light emitting diode to be turned on when the detachable portion is attached to the adapter attaching portion; and a resistor arranged in a space formed in the endoscope adapter to determine a type of the endoscope adapter.

The above and other objects, features and advantages of the invention will become more clearly understood from the following description referring to the accompanying drawings.

DETAILED DESCRIPTION OF THE PREFERRED EMBODIMENTS

In the following, embodiments according to the present invention will be described with reference to the accompanying drawings.

Figure 1:
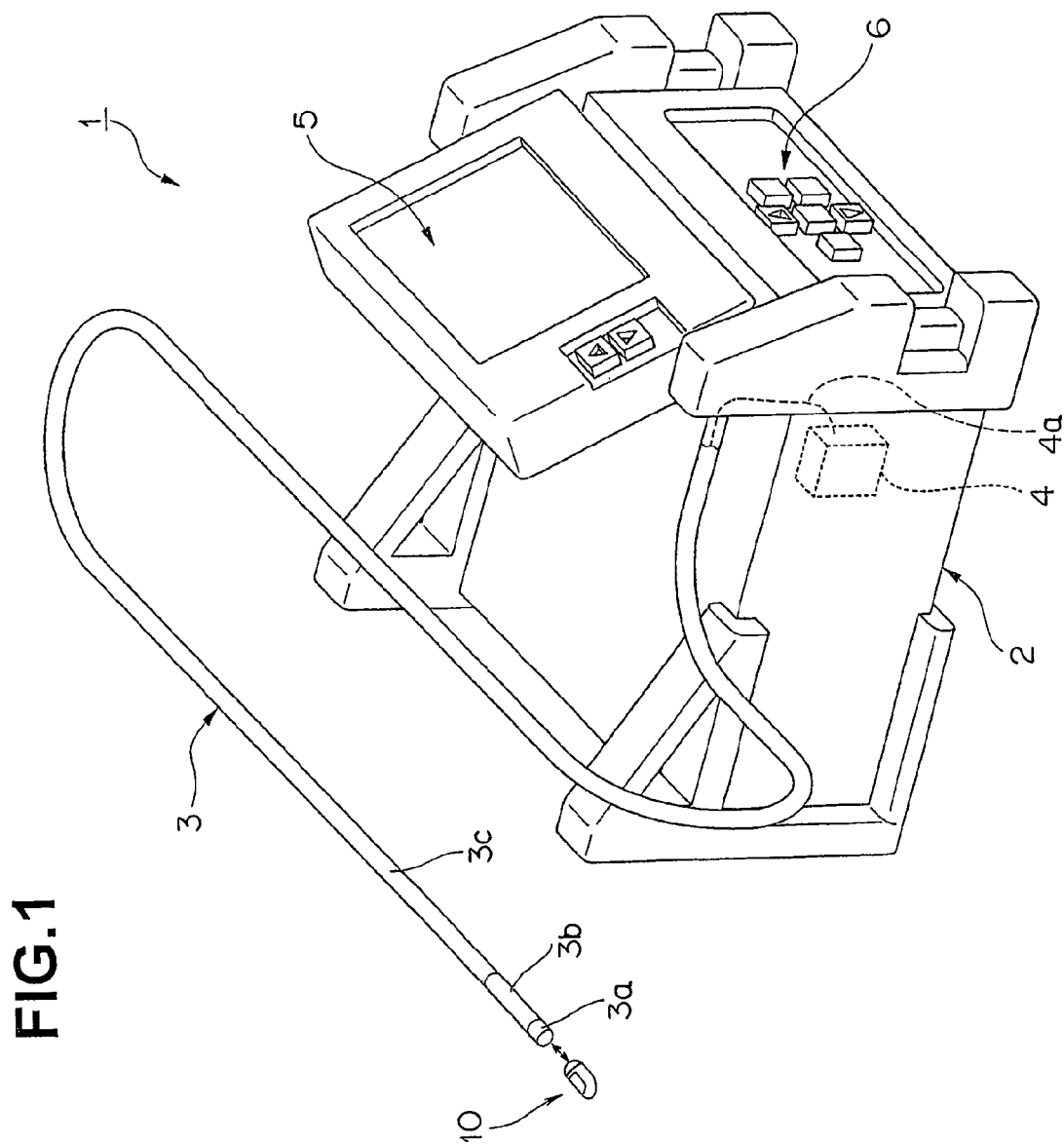
FIG. 1 is a figure explaining an adapter type endoscope apparatus.

As shown in FIG. 1, an adapter type endoscope apparatus 1 is configured by including an endoscope main body portion 2, a long endoscope insertion portion (hereinafter abbreviated as insertion portion) 3 provided, for example, with a bending portion 3b, and a distal end adapter 10 as an endoscope adapter. An adapter type endoscope is configured by attaching the distal end adapter 10 to a distal end portion 3a (as will be described below) of the insertion portion 3.

The endoscope main body portion 2 is formed in a substantially box shape, and a control portion 4, and the like, is provided inside the endoscope main body portion 2. A monitor 5 for displaying an endoscopic image, and the like, is provided, for example, on the front surface side of the top surface portion of the endoscope main body portion 2. Further, an operation panel 6 for performing the bending operation of the bending portion 3b provided in the insertion portion 3, and the like, are provided on the front surface of the endoscope main body portion 2.

The insertion portion 3 is configured by providing successively from the distal end side, the insertion portion distal end portion (hereinafter abbreviated as distal end portion) 3a, the bending portion 3b, and a flexible tube portion 3c. The insertion portion 3 is configured such that the proximal end portion thereof is electrically and mechanically connected to the endoscope main body portion 2 via a connecting portion (not shown). The distal end portion 3a has in the inside thereof an image-forming optical system as will be described below.

The distal end adapter 10 is configured so as to be detachably attached to the distal end portion 3a. In the present embodiment, the distal end adapter 10 is a side view type configured to observe a direction perpendicular to the longitudinal axis direction of the insertion portion 3, that is, a so-called side view direction, and includes a side view optical system (as will be described below) as an adapter side observation optical system.

Figure 2:
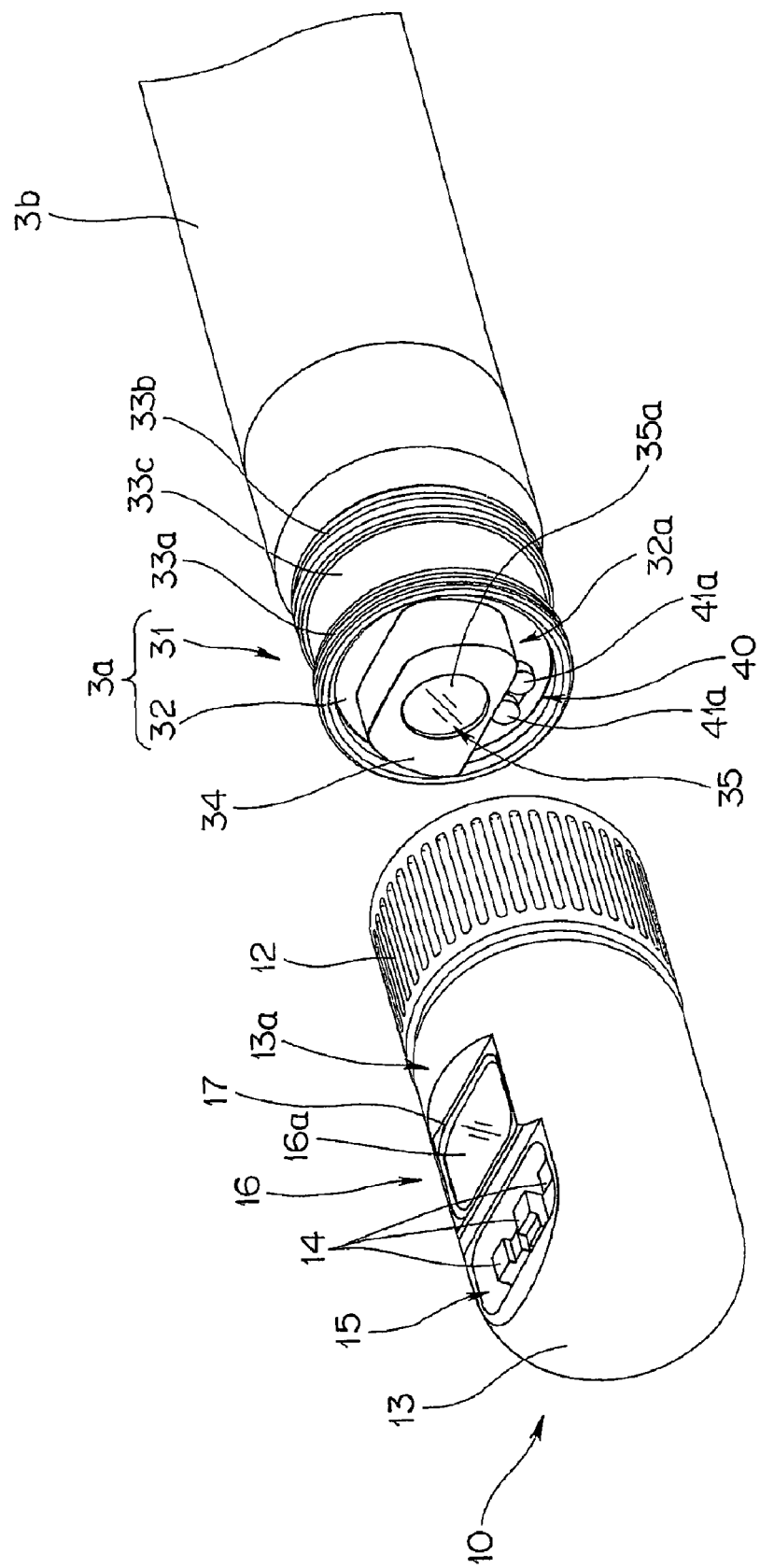
FIG. 2 is a figure explaining an insertion portion distal end portion of the adapter type endoscope, and a side view type distal end adapter which can be detachably attached to the insertion portion distal end portion.
Figure 3:
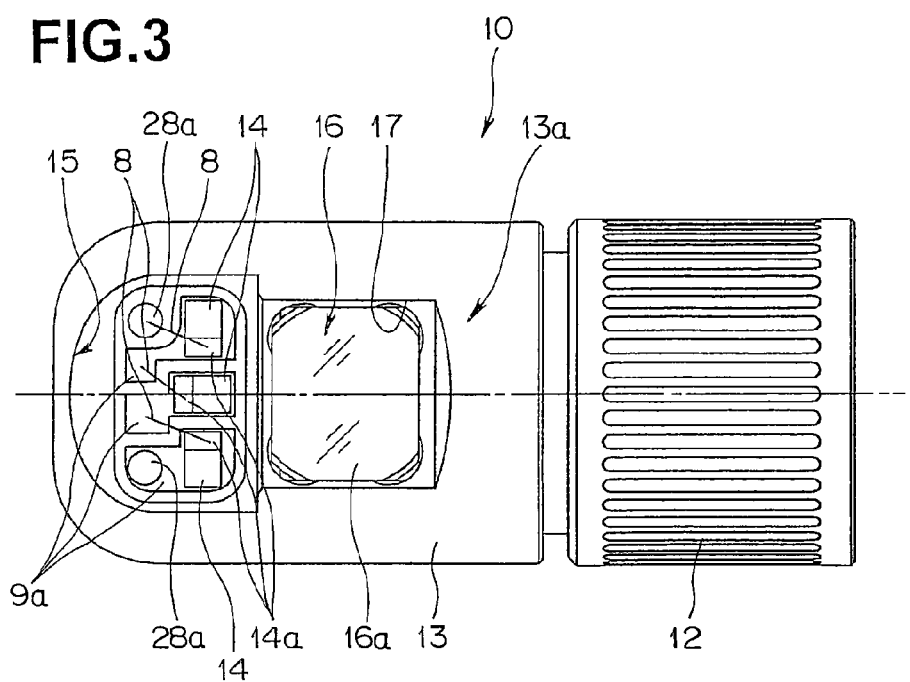
FIG. 3 is a plan view when the side view type distal end adapter is viewed from the observation window side.
Figure 5:
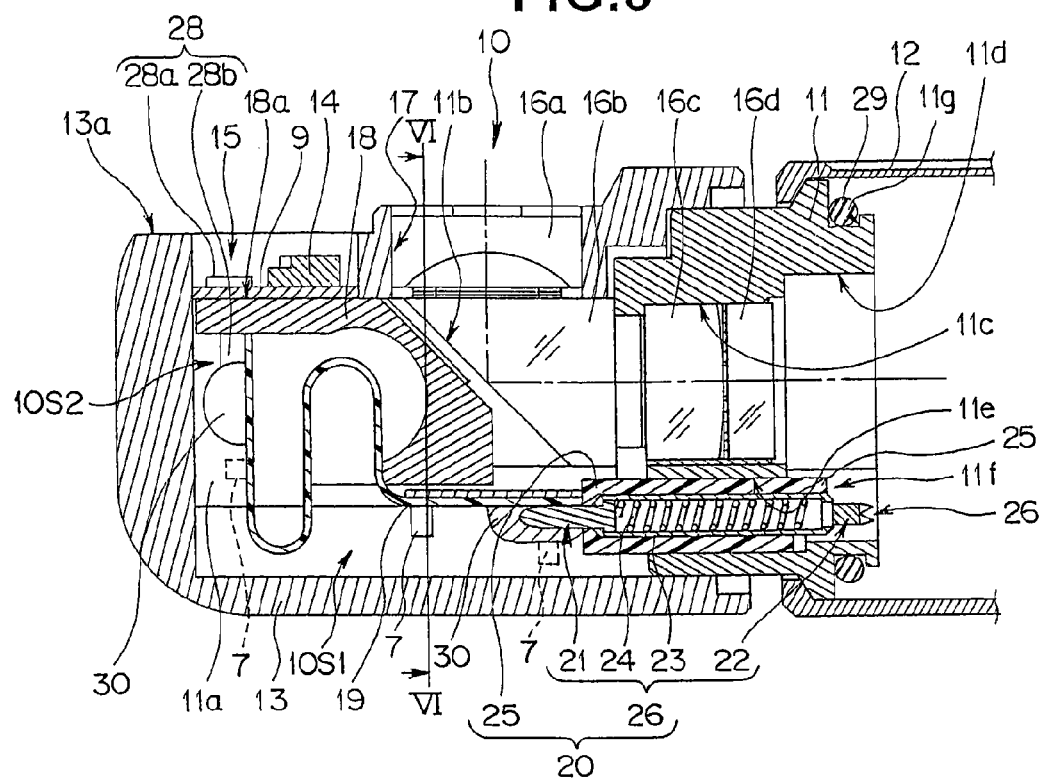
FIG. 5 is a sectional view along the line V-V in FIG. 4.

As shown in FIG. 2 and FIG. 3, the distal end adapter 10 is mainly configured by including a detachable ring 12, a hood portion 13, and an adapter main body 11 which will be described below and is shown in FIG. 5. The hood portion 13 is a substantially cylindrical exterior member whose distal end portion is formed as a curved surface. An illumination hole 15 and an optical portion hole 17 are formed on the side of one side surface 13a of the hood portion 13. A plurality of light emitting devices, such as for example, LED chips (hereinafter abbreviated as LEDs) 14 faces the illumination hole 15. An observation window 16a, which configures a side view optical system 16, is arranged in the optical portion hole 17.

Figure 17:
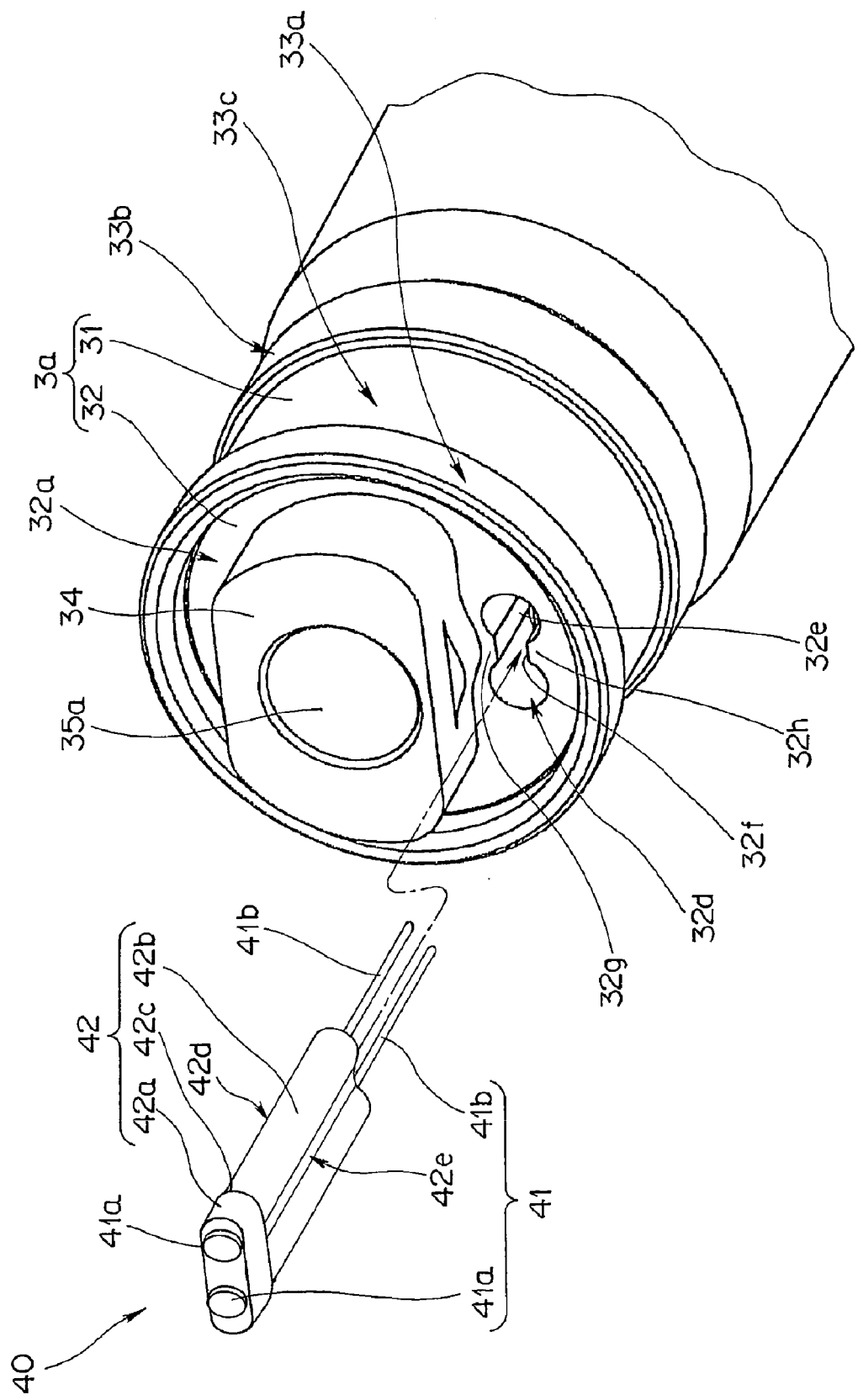
FIG. 17 is a figure explaining a relationship between the endoscope side electrical connection portion and the endoscope side connection portion arrangement hole.

On the other hand, as shown in FIG. 2 and FIG. 17, the distal end portion 3a of the insertion portion 3 is mainly configured by an exterior portion 31 and a distal end portion main body 32. The exterior portion 31 has an adapter attaching portion on a distal end side of an outer peripheral surface thereof. The adapter attaching portion includes a first male screw portion 33a which is projectingly provided, and includes at a proximal end side thereof a second male screw portion 33b which is projectingly provided. The first male screw portion 33a is formed narrower than the second male screw portion 33b. A sliding portion 33c is formed between the first male screw portion 33a and the second male screw portion 33b.

A rotation stopping portion 34 and contact surface portions 41a of a pair of terminal members 41, and the like, are projectingly provided on a distal end surface 32a of the distal end portion main body 32. The pair of terminal members 41 configure a conductive portion of an endoscope side electrical connection portion (hereinafter abbreviated as endoscope side connection portion) 40. The rotation stopping portion 34 is configured as a projecting portion having a substantially D-shaped cross section. That is, the rotation stopping portion 34 is provided with plane portions which face each other and configure side surfaces, and with curved surface portions which connect the plane portions to each other. The rotation stopping portion 34 serves as a positioning mechanism for positioning the distal end adapter 10 attached to the distal end portion 3a, and also serves as a protection mechanism for protecting the contact surface portion 41a of the terminal member 41. Note that reference character 35a denotes a distal end lens cover which is provided for protecting an image-forming optical system 35.

In the following, the configurations of the distal end adapter 10 and the distal end portion 3a will be specifically described, respectively.

First, the distal end adapter 10 will be described with reference to FIGS. 4 to 12.

Figure 4:
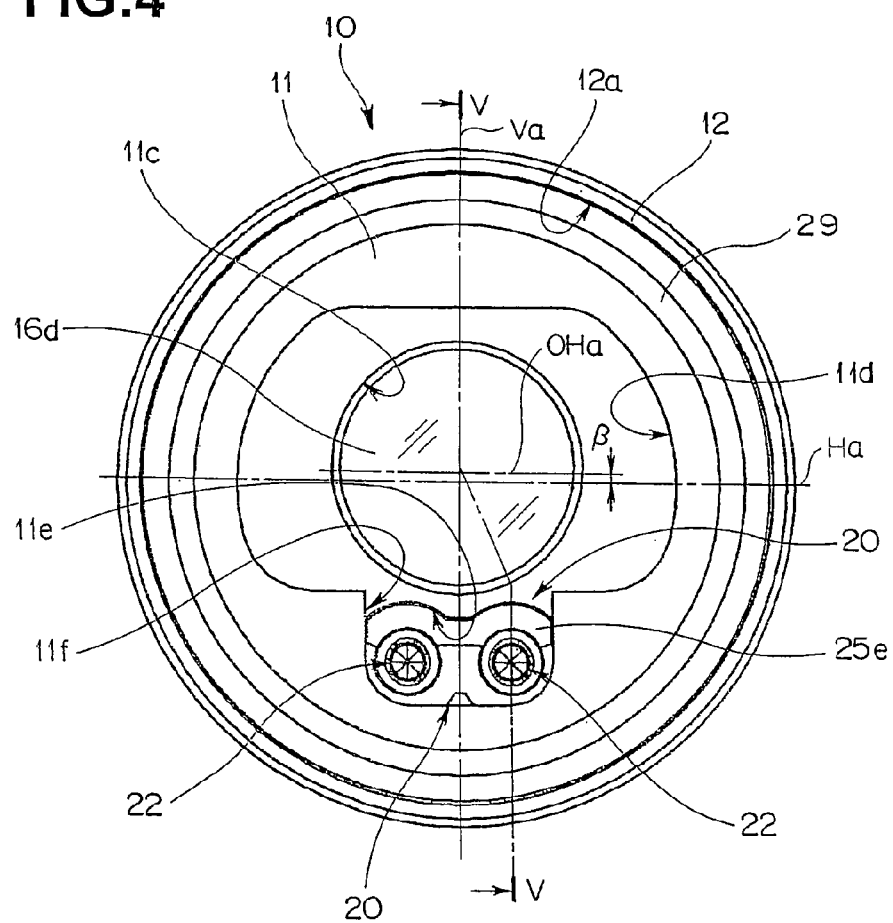
FIG. 4 is a plan view when the side view type distal end adapter is viewed from the opening side of a detachable ring.

As shown in FIG. 4, the distal end adapter 10 is configured symmetrically with respect to the vertical axis Va as the center line in the figure. As shown in FIG. 5, the distal end adapter 10 is configured by including the adapter main body 11, the detachable ring 12, the hood portion 13, an LED holding plate 18, a flexible substrate 19, an adapter side electrical connection portion (hereinafter abbreviated as adapter side connection portion) 20, and the like.

Figure 10:
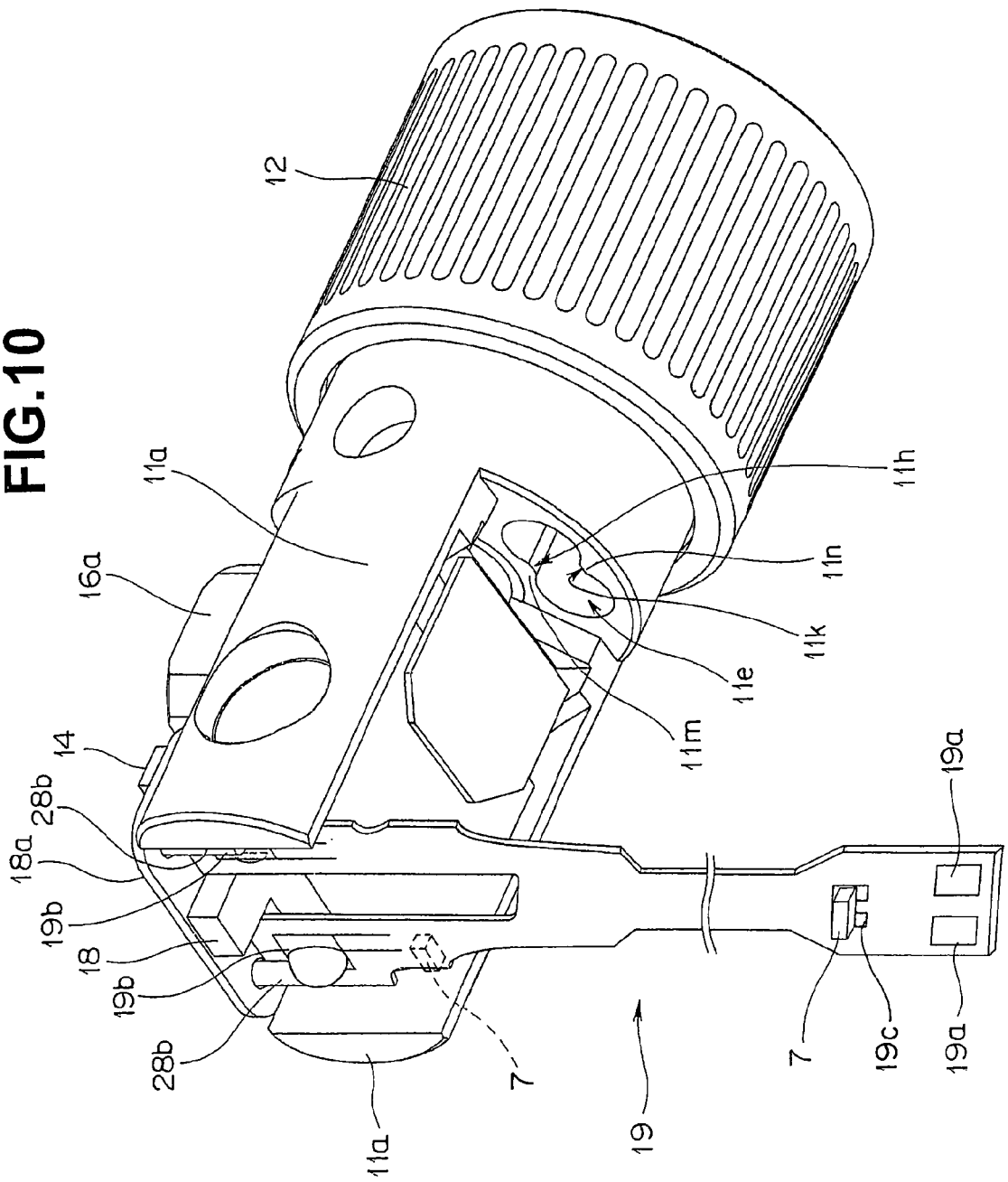
FIG. 10 is a figure explaining a configuration of a flexible substrate, and an opening shape of an adapter side connection portion arrangement hole.
Figure 11:
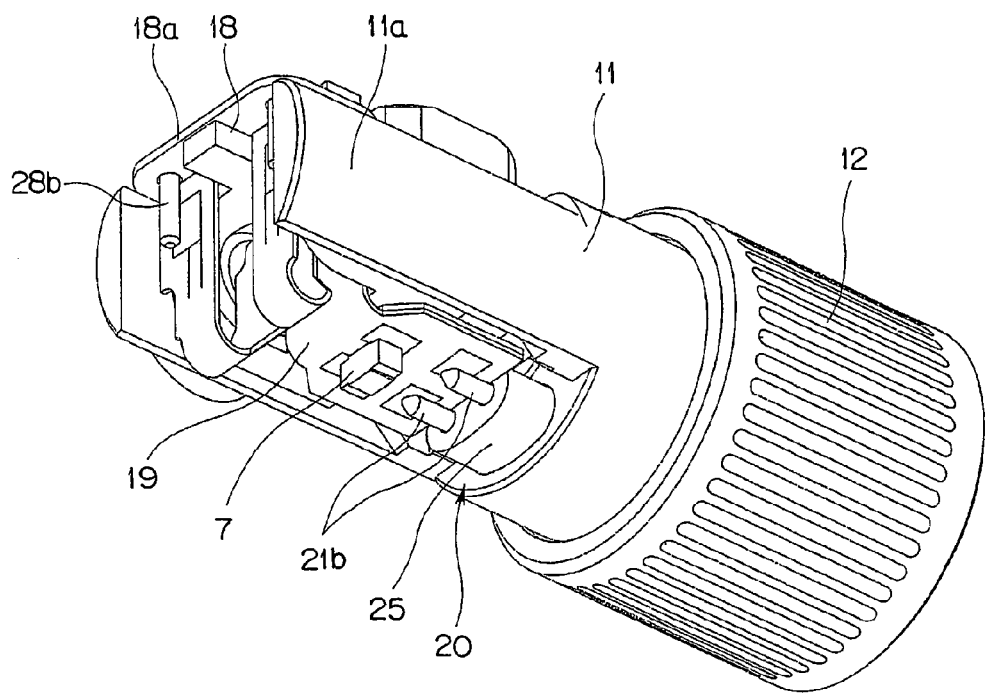
FIG. 11 is a figure explaining a state where a first pin member of the adapter side electrical connection portion fixed to the adapter side connection portion arrangement hole is electrically connected to an LED electrode by the flexible substrate.
Figure 12:
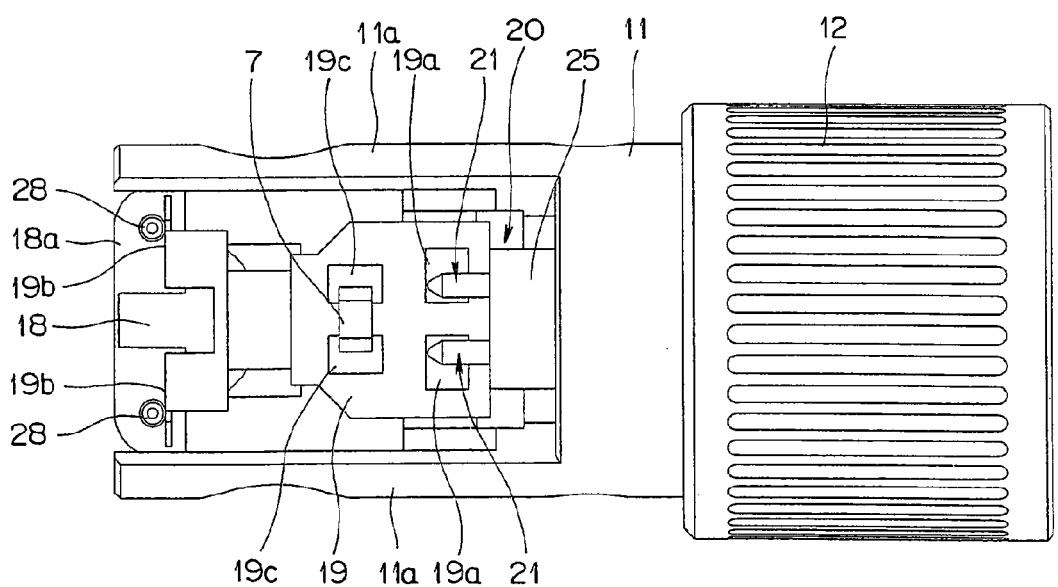
FIG. 12 is a plan view when the side view type distal end adapter in a state where a hood portion is removed, is viewed from the other surface side facing the one surface side.

The adapter main body 11 is an apparatus main body, which has a cylindrical shape formed of, for example, a metal member as a rigid member and is provided with a projecting portion 11a at the distal end side of the cylindrical shape. The projecting portion 11a is configured by forming one end of the adapter main body 11 in a shape of a pair of projections as will be described below and as shown in FIGS. 10 to 12. As shown in FIG. 5, in the adapter main body 11, there are formed a supporting portion 11b, an optical hole 11c, a positioning hole 11d, and an adapter side connection portion arrangement hole (hereinafter abbreviated first connection portion hole) 11e, in addition to the projecting portion 11a.

A prism 16b which configures the side view optical system 16 is provided on the supporting portion 11b. A first optical lens 16c, a second optical lens 16d, a space ring, a diaphragm, and the like, are arranged in the optical hole 11c. The opening shape of the positioning hole 11d has the same approximate D shape as the external shape of the rotation stopping portion 34, and the rotation stopping portion 34 is inserted into the positioning hole 11d. An abutting pin arrangement recessed portion 11f is provided on the side of the first connection portion hole 11e of the positioning hole 11d. The adapter side connection portion 20 is fixed in the first connection portion hole 11e of the positioning hole 11d. The opening shape of the first connection portion hole 11e is a shape of the horizontally oriented figure of 8 as will be described below and as shown in FIG. 10. Reference numeral 29 denotes an O ring and is arranged in a circumferential groove 11g formed on the proximal end side of the adapter main body 11.

As shown in FIG. 4, the detachable ring 12, which is a detachable portion and has a substantially tubular shape, is formed concentrically to the adapter main body 11, so as to be rotatably connected to the adapter main body 11. On the proximal end side inner peripheral surface of the detachable ring 12, as shown in FIG. 2, there is provided a female screw portion 12a into which the male screw portions 33a and 33b are screwed.

As shown in FIG. 5, the hood portion 13 is an exterior member, at the distal end portion of which the curved surface portion is formed as described above. The opening on the side of the proximal end portion of the hood portion 13 is fixed integrally to the adapter main body 11, for example, by adhesion. LEDs 14 mounted on the LED holding plate 18 are arranged in the illumination hole 15 having an opening on the side of the one side surface 13a of the hood portion 13. Further, the observation window 16a, a space ring, a diaphragm, and the like, which configure the side view optical system 16 are fixed in the optical portion hole 17 having an opening on the side of the one side surface 13a of the hood portion 13.

The LED holding plate 18 is arranged integrally with the distal end surface side portion of the adapter main body 11. A substrate 9 is arranged on a substrate arrangement surface 18a of the LED holding plate 18. A pattern 9a, for example, as shown in FIG. 3 is formed beforehand on the substrate 9. On the substrate 9, there are mounted the LEDs 14 and a pair of LED electrodes 28 as element electrodes. Wiring members 8 are respectively electrically connected between a head portion 28a of the LED electrode 28 provided on the substrate 9 and a contact portion 14a of the LED 14, and between the pattern 9a and a contact portion 14a of the LED 14. Reference numeral 28b denotes a pin portion of the LED electrode 28, and one end side of the flexible substrate 19 is electrically connected to the pin portion 28b.

The adapter side connection portion 20 will be described with reference to the drawings.

Figure 7:
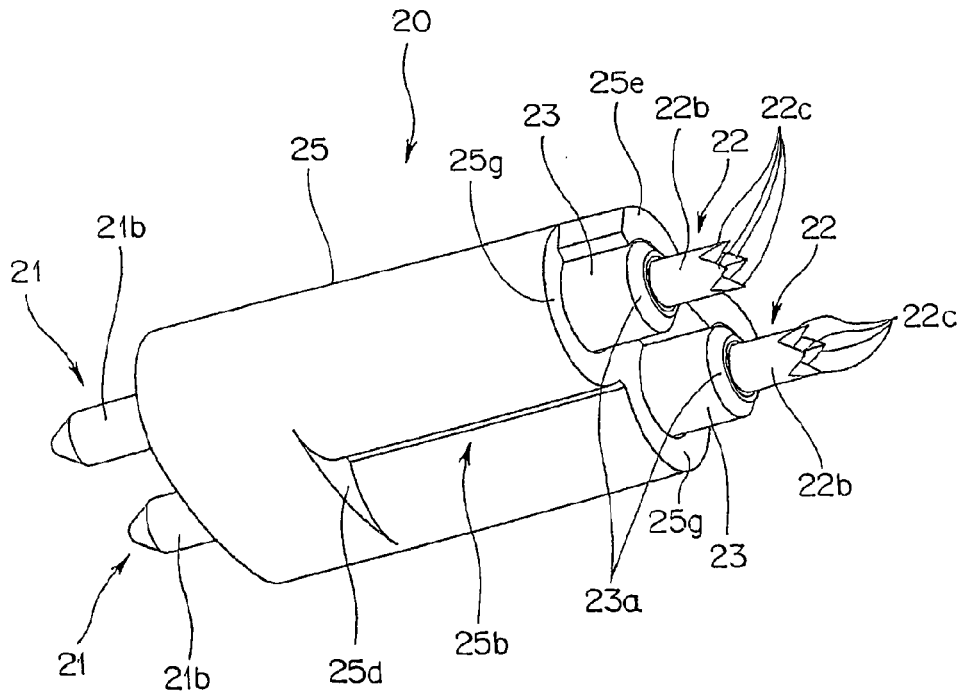
FIG. 7 is a perspective view explaining an adapter side electrical connection portion.
Figure 9:
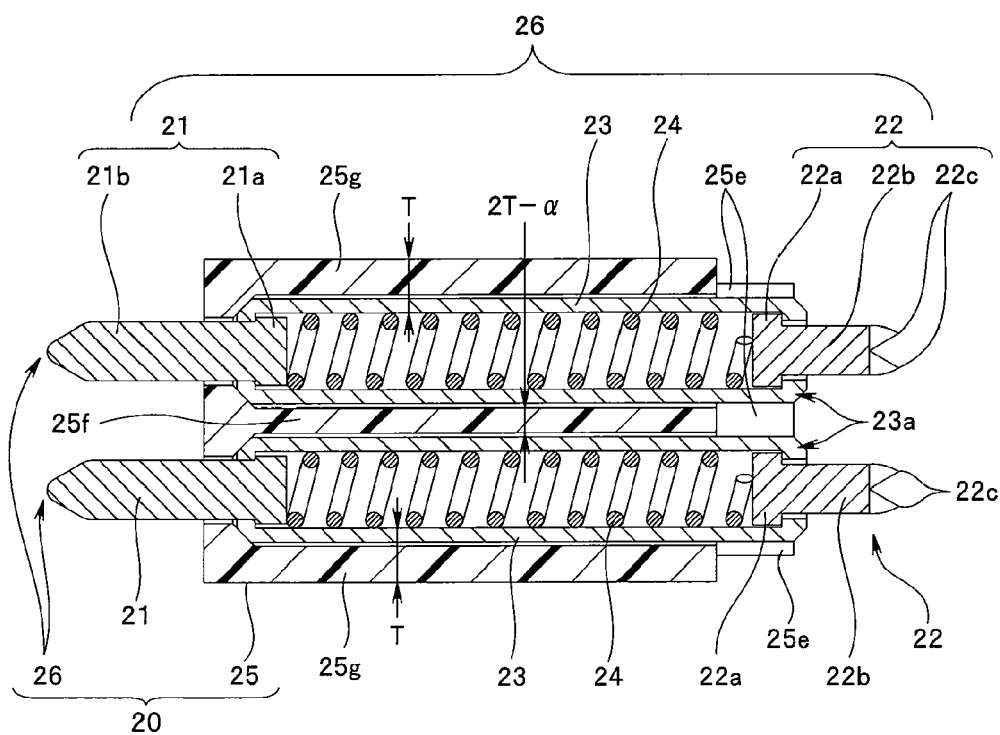
FIG. 9 is a sectional view along the line IX-IX in FIG. 8.

As shown in FIG. 5, FIG. 7, and FIG. 9, the adapter side connection portion 20 is a contact pin unit which is configured by a pair of case bodies 23, first pin members 21 configuring a contact pin, second pin members 22 configuring an abutting pin, coil springs 24 serving as an urging member, and an adapter side insulating portion 25 configuring an outer sheath. The first pin member 21, the second pin member 22, the case body 23, and the coil spring 24 are conductive members which are formed of aluminum, brass, iron, or the like, and the surface of which is plated with a high conductivity material such as gold. The reference character 26 denotes an electrical connection member which is configured by arranging the first pin member 21, the second pin member 22 and the coil spring 24 in the case body 23.

The adapter side insulating portion 25 is formed of a high heat resistance resin member, and integrally covers a pair of electrical connection members 26 so as to insulate the pair of electrical connection members 26 as conductive portions from each other. At the distal end portion of a pin portion 22b of the second pin member 22, there are provided four contact portions 22c having a tapered shape which becomes thinner toward the distal end side. The four contact portions 22c are formed by providing two V-shaped grooves in a cross shape in the pin distal end portion from the side of the distal end surface.

Here, the electrical connection member 26 configured by the first pin member 21, the second pin member 22, the case body 23, and the coil spring 24 is described.

The first pin member 21 is arranged on the distal end side of the case body 23. The first pin member 21 is provided with a flange portion 21a, and the flange portion 21a is fixed integrally with the case body 23 by, for example, a conductive adhesive. In the fixed state, a pin portion 21b of the first pin member 21 is in the state of projecting from the distal end side of the case body 23 by a predetermined amount. The coil spring 24 is slidably arranged in the case body 23 to which the first pin member 21 is fixed. One end side of the coil spring 24 is arranged in contact with the proximal end surface of the flange portion 21a which configures the first pin member 21. The second pin member 22 is slidably arranged in the case body 23 in which the coil spring 24 is arranged. In this arrangement state, the distal end surface of a flange portion 22a of the second pin member 22 is arranged in contact with the proximal end side of the coil spring 24. In this arrangement state, a caulked portion 23a configured by bending the entire periphery of the proximal end portion of the case body 23 in the center axis direction is provided at a predetermined position. By providing the caulked portion 23a, the second pin member 22 of the electrical connection member 26 is urged by the urging force of the coil spring 24 in the axis direction, and the pin portion 22b of the second pin member 22 projects from the proximal end side of the case body 23 by a predetermined amount. The caulked portion 23a in the electrical connection member 26 is to prevent the second pin member 22 from falling off. The second pin member 22 which is in the projecting state by being urged by the coil spring 24, is slidable in the axis direction.

The adapter side connection portion 20 is configured in a state where the pair of electrical connection members 26 are arranged in parallel with each other at a predetermined interval. The electrical connection members 26 arranged in the adapter side connection portion 20 are covered by the adapter side insulating portion 25, so as to be insulated from each other by the adapter side insulating portion 25. In the present embodiment, the adapter side connection portion 20 is specifically configured by insert molding. For this reason, the end portion of the first pin member 21 covered by the adapter side insulating portion 25 is set in the state of projecting from the one end surface of the adapter side insulating portion 25 by a predetermined amount. Further, the end portion of the second pin member 22 covered by the adapter side insulating portion 25 is set in the state of projecting from the other end surface of the adapter side insulating portion 25 by a predetermined amount.

Figure 8:
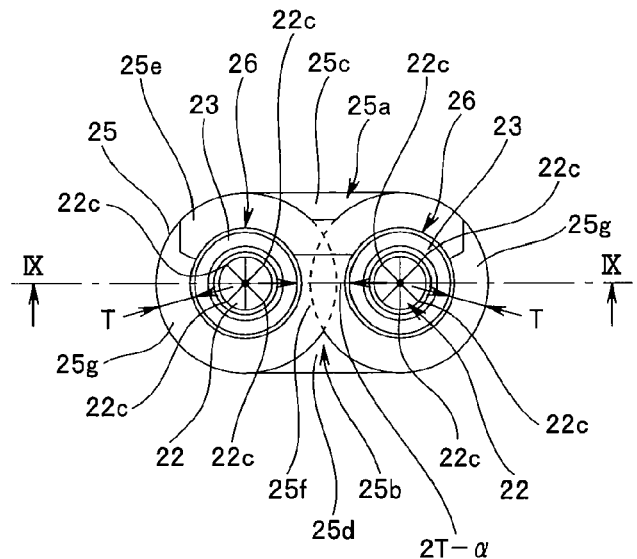
FIG. 8 is a front view when the adapter side electrical connection portion is viewed from the side of a second pin member.

As shown in FIG. 5 and FIGS. 7 to 9, the adapter side insulating portion 25 is configured by including an eaves portion 25e on the side of the second pin member 22. As shown in FIG. 8, the eaves portion 25e is provided so as to cover the one surface side (the upper side in the figure) of the pair of case bodies 23. The eaves portion 25e prevents a trouble caused by the case body 23 electrically contacting the rotation stopping portion 34.

As shown in FIG. 8 and FIG. 9, the adapter side insulating portion 25 is provided over the entire periphery of the case body 23 which configures the electrical connection member 26 of the adapter side connection portion 20. The thickness of the adapter side insulating portion 25 covering the case body 23 is set to a dimension T except for the portion in which the electrical connection members are adjacent to each other.

Specifically, the thickness of an inter-pin adapter side insulating portion 25f which is an inter-pin insulating portion on a line perpendicular to the center axes of the pair of electrical connection members 26 configuring the adapter side connection portion 20, in other words, the thickness of the inter-pin adapter side insulating portion 25f which is provided between the case bodies 23 of the electrical connection members 26 arranged adjacent to each other, is set to a dimension smaller than twice the thickness T (described as 2T—α in the figure) of a circumferential insulating portion 25g which configures the adapter side insulating portion 25 covering the periphery of the case body 23.

In the present embodiment, the thickness dimension of the inter-pin adapter side insulating portion 25f is reduced to be smaller than twice the thickness T of the circumferential insulating portion 25g, and the interval between the pair of adjacent electrical connection members 26 is reduced as much as possible within a range in which the insulating state can be maintained.

In this way, the adapter side connection portion 20 having an integral configuration is configured in such a way that the pair of electrical connection members 26, each of which is configured by arranging the first pin member 21, the second pin member 22, and the coil spring 24 in the case body 23, are provided in the adapter side insulating portion 25, so as to be in parallel with each other at a predetermined interval. Then, in this configuration, the thickness of the inter-pin adapter side insulating portion 25f on the line perpendicular to the center axes of the pair of electrical connection members 26 of the adapter side connection portion 20 is set to a dimension smaller than the thickness 2T of the circumferential insulating portion 25g.

As a result, the thickness of the insulating portion connecting between the center axes of the pair of electrical connection members 26 provided in the adapter side connection portion 20 is made smaller by a than the thickness in the case where the two electrical connection members 26, which are respectively provided with the adapter side insulating portion 25 having the thickness T around the periphery of the case body 23, are arranged side by side. Specifically, the thickness dimension of the adapter side insulating portion 25 in the case where the pair of electrical connection members 26 provided with the adapter side insulating portion 25 having the thickness T are arranged side by side, becomes 4T as a whole, while the thickness of the insulating portion on the line connecting between the center axes of the pair of electrical connection members 26 provided in the adapter side connection portion 20 can be made smaller than 4T by a.

Therefore, in the adapter side connection portion 20 configured such that the pair of electrical connection members 26 are arranged in parallel with the other at a predetermined interval so as to be integrated by providing the adapter side insulating portion 25, the thickness of the inter-pin adapter side insulating portion 25f is set smaller than 2T, so as to thereby reduce the longitudinal width dimension of the adapter side connection portion 20. As a result, it is possible to further reduce the diameter of the distal end adapter 10.

Further, the adapter side connection portion 20 in which the pair of electrical connection members 26 are integrally configured, is arranged on the lower side from the horizontal axis Ha of the distal end adapter 10 as shown in FIG. 4. In the configuration in which two electrical connection members are respectively arranged on both sides of the horizontal axis Ha, the optical axis horizontal axis OHa of the optical hole 11c cannot be arranged eccentrically upward by β in the figure with respect to the horizontal axis Ha. However, with the above described configuration, the optical axis horizontal axis OHa of the optical hole 11c can be arranged eccentrically upward by β in the figure with respect to the horizontal axis Ha, and thereby the diameter of the distal end portion 3a can be reduced.

As shown in FIG. 4, FIG. 7, and FIG. 8, a first recessed portion 25a and a second recessed portion 25b having an abutting surface 25d are provided on the side surface portion of the adapter side insulating portion 25 which configures the adapter side connection portion 20. The first recessed portion 25a has a predetermined recessed shape which is opened on the proximal end surface side, and has an abutting surface 25c in an intermediate portion between the proximal end surface side and the distal end side. Similarly to the first recessed portion 25a, the second recessed portion 25b has a predetermined recessed shape which is opened on the proximal end surface side, and has the abutting surface 25d in the intermediate portion. As shown in FIG. 8, the first recessed portion 25a and the second recessed portion 25b are formed in an opposing positional relationship substantially at the center of both the planar shaped side surfaces positioned one above the other in the figure, that is, between the electrical connection members.

The abutting surfaces 25c and 25d are positioning surfaces for setting the arrangement position of the adapter side connection portion 20. The abutting surfaces 25c and 25d are respectively brought into contact, as will be described below and as shown in FIG. 10, with an abutting end surface 11m which is a positioning portion of projecting portion 11h, and with an abutting end surface 11n which is a positioning portion of a projecting portion 11k. The forming positions of the abutting surfaces 25c and 25d are set so that the distance from the distal end surface of one of the first pin members 21 to the abutting surface 25c is equal to the distance from the distal end surface of the other of the first pin members 21 to the abutting surface 25d. In other words, the abutting surfaces 25c and 25d are end surfaces of the recessed portions 25a and 25b which are formed in the intermediate portion of the side surface portion of the adapter side insulating portion 25 at the same distance from the proximal end side end surface of the adapter side insulating portion 25.

Also, when the adapter side insulating portion 25 of the adapter side connection portion 20 is viewed from the front surface side in the state where the contact portions 22c of the pair of second pin members 22 are set to face the front surface, the external shape of the adapter side insulating portion 25 on the side of the second pin members 22 is an approximate figure-of-8 shape. On the other hand, when the adapter side insulating portion 25 of the adapter side connection portion 20 is viewed from the front surface side in the state where the distal ends of the pair of first pin members 21 are set to face the front surface, the external shape of the adapter side insulating portion 25 on the side of the first pin members 21 is an approximate elliptic shape, in other words, a figure-of-0 shape.

Note that the shape of the first recessed portion 25a and the shape of the second recessed portion 25b are made different from each other so as to prevent the reverse assembling, and are configured such that the projecting portion 11h is inserted and arranged in the first recessed portion 25a, and the projecting portion 11k is inserted and arranged in the second recessed portion 25b.

The adapter side connection portion 20 is fixed in the first connection portion hole 11e shown in FIG. 10. The opening shape of the first connection portion hole 11e is an approximate figure-of-8 shape, which shape is arranged in parallel with the horizontal axis Ha. The first connection portion hole 11e is formed by including the first projecting portion 11h and the second projecting portion 11k which project in the central direction of the hole and are in parallel with the longitudinal axis.

When the adapter side connection portion 20 is inserted and arranged in the first connection portion hole 11e, the first projecting portion 11h of the first connection portion hole 11e is inserted into the first recessed portion 25a on the side of the second pin member 22 of the adapter side connection portion 20. Further, the second projecting portion 11k of the first connection portion hole 11e is inserted into the second recessed portion 25b of the adapter side connection portion 20.

In this insertion state, the adapter side connection portion 20 is pushed into the first connection portion hole 11e. Then, after the second pin member 22 is made to project from the proximal end side opening, the abutting end surface 11m of the first projecting portion 11h is brought into contact with the abutting surface 25c, and the abutting end surface 11n of the second projecting portion 11k is brought into contact with the abutting surface 25d. Thereby, the adapter side connection portion 20 is arranged in the first connection portion hole 11e in a predetermined state. In this arrangement state, the second pin member 22 of the adapter side connection portion 20 is arranged at a predetermined position in the abutting pin arrangement recessed portion 11f in a predetermined state.

The flexible substrate 19 electrically connects the pair of first pin members 21 to the pin portions 28b of the pair of LED electrodes 28. To this end, a pair of first contact portions 19a for electrical connection with the pair of first pin members 21, and a pair of second contact portions 19b for electrical connection with the pair of pin portions 28b, are provided on the respective end portion sides of the flexible substrate 19. The interval between the first contact portions 19a is configured so as to correspond to the adapter side connection portion 20 which is a member for effecting the reduction in the diameter. The interval between the second contact portions 19b is set larger so as to correspond to the arrangement position of the pattern 9a and the LED electrodes 28 which are arranged in consideration of the workability at the time of connecting the wiring member 8, and the like. That is, the interval between the second contact portions 19b is formed larger than the interval between the first contact portions 19a.

Figure 6:
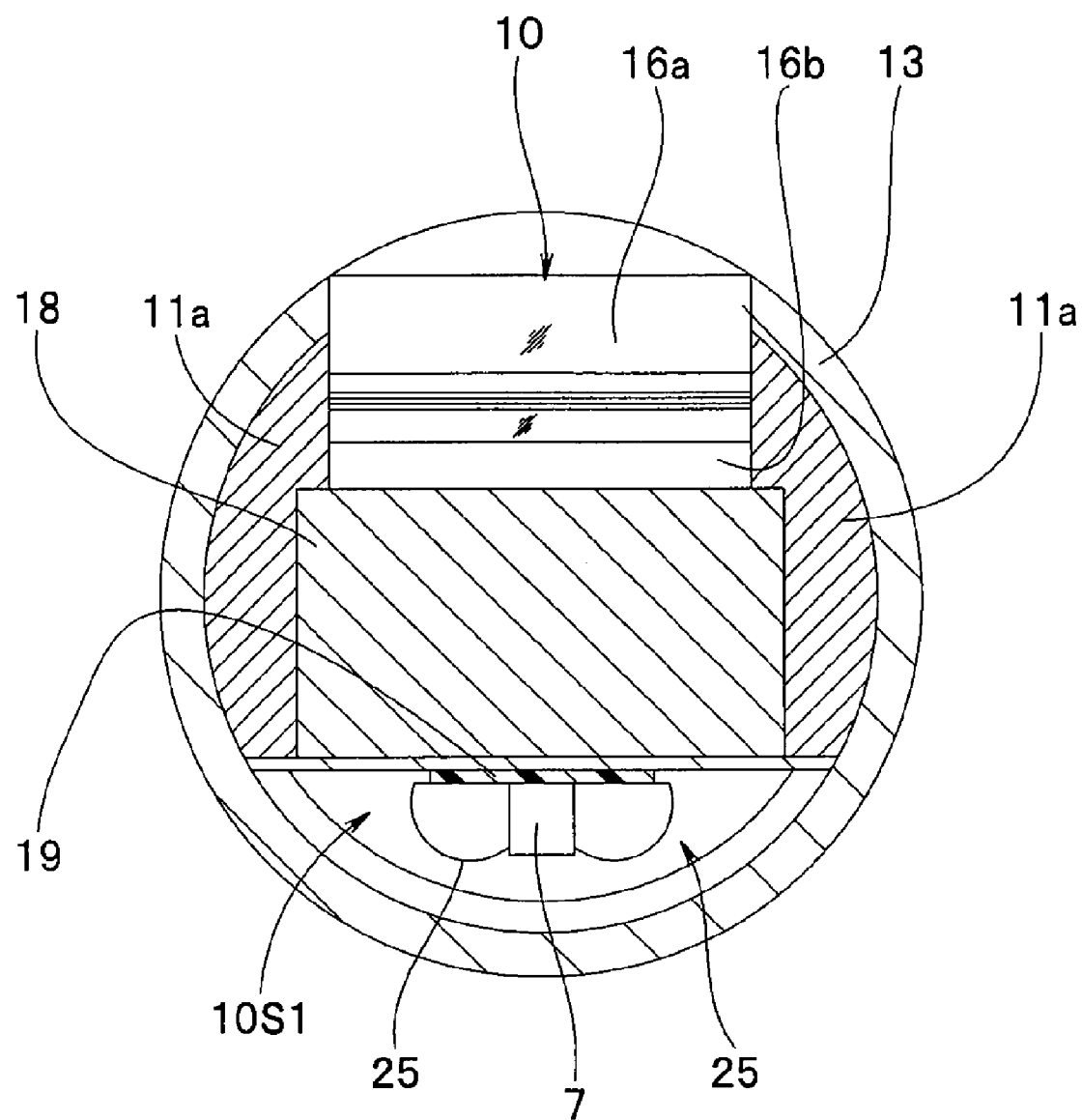
FIG. 6 is a sectional view along the line VI-VI in FIG. 5.

The distal end adapter 10 is provided with a resistor 7 for determining the type of the distal end adapter. Specifically, as shown in FIGS. 5 and 6, the resistor 7 is arranged in a D-shape space 10S1 configured of the hood portion 13 and the LED holding portion 18 so as to face an inner surface of the hood portion 13 of the flexible substrate 19. The mounting position of the resistor 7 on the flexible substrate 19 is not limited in the D-shape space 10S1, and may be in a distal end side space 10S2 configured of the hood portion 13 and the LED holding plate 18 as shown by the dashed lines, for example.

The resistor 7 is mounted on a resistor contact 19c formed on the flexible substrate 19 shown in FIG. 10. The resistor 7 of different resistance value is mounted for each type of the distal end adapter.

The resistor for determining the type of the distal end adapter is thus mounted on the flexible substrate electrically connecting the pair of first pin members and the pin portions of the pair of LED electrodes. The resistor mounted on the flexible substrate is arranged in the D-shape space or in the distal end side space. This prevents accidental contact of the resistor with other electronic components and bad electrical contact of the resistor.

In addition, the resistor is mounted on the flexible substrate so as to face the inner surface of the hood portion, which enables an assembly worker (hereinafter abbreviated as worker) to visually recognize a resistance value of the resistor at the time of assembly work for integrally fixing the adapter main body to the hood portion. As a result, wrong assembly can be prevented.

Note that, as shown by the dashed lines in FIG. 5, the resistor 7 may be electrically connected to the first pin member 21. Furthermore, in addition to the resistor 7, an electric element such as a temperature sensor may be arranged on the flexible substrate 19.

Here, a method for attaching the adapter side connection portion 20 to the adapter main body 11 will be described with reference to FIGS. 10 to 12.

When the adapter side connection portion 20 is attached to the adapter main body 11, the worker applies an adhesive to the plane surface side and the curved surface side of the adapter side insulating portion 25, which are the side surface portion of the adapter side connection portion 20. Then, as described above, the worker inserts the side of the second pin member 22 of the adapter side connection portion 20 from the distal end side opening of the first connection portion hole 11e shown in FIG. 10. At this time, the worker makes the first projecting portion 11h inserted in the first recessed portion 25a, and makes the second projecting portion 11k inserted in the second recessed portion 25b.

And in this inserted state, the worker pushes the adapter side connection portion 20 into the first connection portion hole 11e, so as to bring the abutting surface 25c into contact with the abutting end surface 11m of the first projecting portion 11h, and to bring the abutting surface 25d into contact with the abutting end surface 11n of the second projecting portion 11k. Then, the worker holds the contact state of the abutting surfaces 25c and 25d of the adapter side connection portion 20 with the abutting end surfaces 11m and 11n until the adhesive is cured.

Thereby, the adapter side connection portion 20 is integrally fixed to the adapter main body 11. At this time, the pin portions 21b of the pair of first pin members 21 are aligned so as to project from the end surface of the distal end side opening to the distal end side by a predetermined amount, and the pin portions 22b of the pair of second pin members 22 are aligned so as to project in the abutting pin arrangement recessed portion 11f from the bottom surface of the abutting pin arrangement recessed portion 11f by a predetermined amount.

Then, as shown in FIG. 11 and FIG. 12, the flexible substrate 19 is bent and housed in the space formed by the projecting portion 11a and the LED holding plate 18. The first contact portions 19a provided on the flexible substrate 19 are arranged in a predetermined state with respect to the pin portions 21b of the respective first pin members 21. Then, one of the pin portions 21b and one of the first contact portions 19a are electrically connected to each other with, for example, solder 30, as shown in FIG. 5. Further, the other of the first pin portions 21b and the other of the first contact portions 19a are electrically connected to each other with solder 30.

In this way, the first connection portion hole 11e whose opening shape is an approximate figure-of-8 shape, is formed in the distal end adapter 10. On the other hand, the first recessed portion 25a having the abutting surface 25c and the second recessed portion 25b having the abutting surface 25d are provided on the side surface portion of the plane surface side of the adapter side insulating portion 25 which configures the adapter side connection portion 20.

Thereby, the external shape of the adapter side insulating portion 25 on the side of the second pin member 22 becomes an approximate figure-of-8 shape which coincides with the opening shape of the first connection portion hole 11e. Also, the respective distances from the abutting surfaces 25c and 25d of the recessed portions 25a and 25b to the distal end of the contact portion 22c of the second pin member 22 are set to be equal to each other, so that the abutting surface 25c and 25d are used as the positioning surfaces.

For this reason, when the adapter side insulating portion 25 having the figure-of-8 shaped portion is inserted and arranged in the first connection portion hole 11e having the figure-of-8 shaped opening, the abutting surface 25c of the first recessed portion 25a is brought into contact with the abutting end surface 11m of the first projecting portion 11h provided in the first connection portion hole 11e, and also the abutting surface 25d of the second recessed portion 25b is brought into contact with the abutting end surface 11n of the second projecting portion 11k provided in the first connection portion hole 11e.

Thereby, the adapter side connection portion 20 is positioned and arranged in the predetermined position with respect to the first connection portion hole 11e of the distal end adapter 10. Further, in this abutting arrangement state, the adapter side connection portion 20 is integrally fixed to the distal end adapter 10, so that the pair of first pin members 21 and the pair of second pin members 22 can be arranged in the predetermined position and in the predetermined projecting state.

That is, in the present embodiment, it is possible for the worker to easily perform a work for arranging the pair of electrical connection members 26 each having the first pin member 21, the second pin member 22, and the like, in the predetermined position and in the predetermined state, by arranging the adapter side connection portion 20 in the first connection portion hole 11e in the predetermined state without arranging the two electrical connection members one by one.

Further, in order to position and arrange the adapter side connection portion 20 in the predetermined position with respect to the first connection portion hole 11e of the distal end adapter 10, the first recessed portion 25a and the second recessed portion 25b which respectively have the end surfaces, are formed in the side surface portion of the adapter side insulating portion 25 of the adapter side connection portion 20, and the end surfaces of the recessed portions 25a and 25b are respectively used as the abutting surfaces 25c and 25d. On the other hand, the first projecting portion 11h which is inserted and arranged in the first recessed portion 25a, and the second projecting portion 11k which is inserted and arranged in the second recessed portion 25b, are provided in the first connection portion hole 11e. Also, the distal end surfaces of the projecting portions 11k and 11h are respectively used as the abutting end surface 11m which is brought into contact with the abutting surface 25c of the first recessed portion 25a, and as the abutting end surface 11n which is brought into contact with the abutting surface 25d of the second recessed portion 25b.

Therefore, when the adapter side connection portion 20 is arranged in the first connection portion hole 11e, the abutting end surface 11m of the first projecting portion 11h is brought into contact with the abutting surface 25c of the first recessed portion 25a, and the abutting end surface 11n of the second projecting portion 11k is brought into contact with the abutting surface 25d of the second recessed portion 25b. Thereby, the adapter side connection portion 20 can be arranged in the state of being positioned.

That is, the adapter side connection portion 20 is positioned and arranged by bringing the abutting end surfaces 11m and 11n into contact with the abutting surfaces 25c and 25d which are configured so as to be recessed from the outer peripheral surface of the adapter side insulating portion 25, without providing a flange portion, or the like, which projects from the outer peripheral surface of the adapter side insulating portion 25 configuring the maximum external shape of the adapter side connection portion 20. Thereby, it is possible to position and arrange the adapter side connection portion 20 in the distal end adapter 10, and to fix the adapter side connection portion 20 to the distal end adapter 10, without largely forming the external shape of distal end adapter 10.

Note that in the above described explanation, it is assumed that the adhesive is applied beforehand to the side surface portions of the plane surface side and the curved surface side of the adapter side insulating portion 25 which configures the adapter side connection portion 20. However, it may also be configured such that after the adapter side connection portion 20 is arranged in the first connection portion hole 11e in the predetermined state, an adhesive having excellent fluidity is poured in the gap between the adapter side connection portion 20 and the first connection portion hole 11e, and thereby the adapter side connection portion 20 and the first connection portion hole 11e are stuck and fixed to each other.

Further, in the above described explanation, it is assumed that after the adapter side connection portion 20 is fixed to the first connection portion hole 11e, the first pin portion 21b and the first contact portion 19a of the flexible substrate 19 are electrically connected to each other. However, it may also be configured such that the adapter side connection portion 20 in the state where the first pin portion 21b is electrically connected to the first contact portion 19a of the flexible substrate 19, is arranged in the first connection portion hole 11e in a predetermined state, and thereafter fixed in this state.

Further, the present embodiment is configured such that the pair of first pin members 21, the pair of second pin members 22, and the like, are provided in the adapter side connection portion 20. However, when three or more of the pin members 21 and 22 are needed, the adapter side connection portion is formed by providing the adapter side insulating portion 25 in the state where a required number of electrical connection members 26 are arranged in parallel with each other at predetermined intervals.

Next, the distal end portion 3a and the endoscope side connection portion 40 fixed to the distal end portion 3a will be described with reference to FIGS. 13 to 17.

Figure 13:
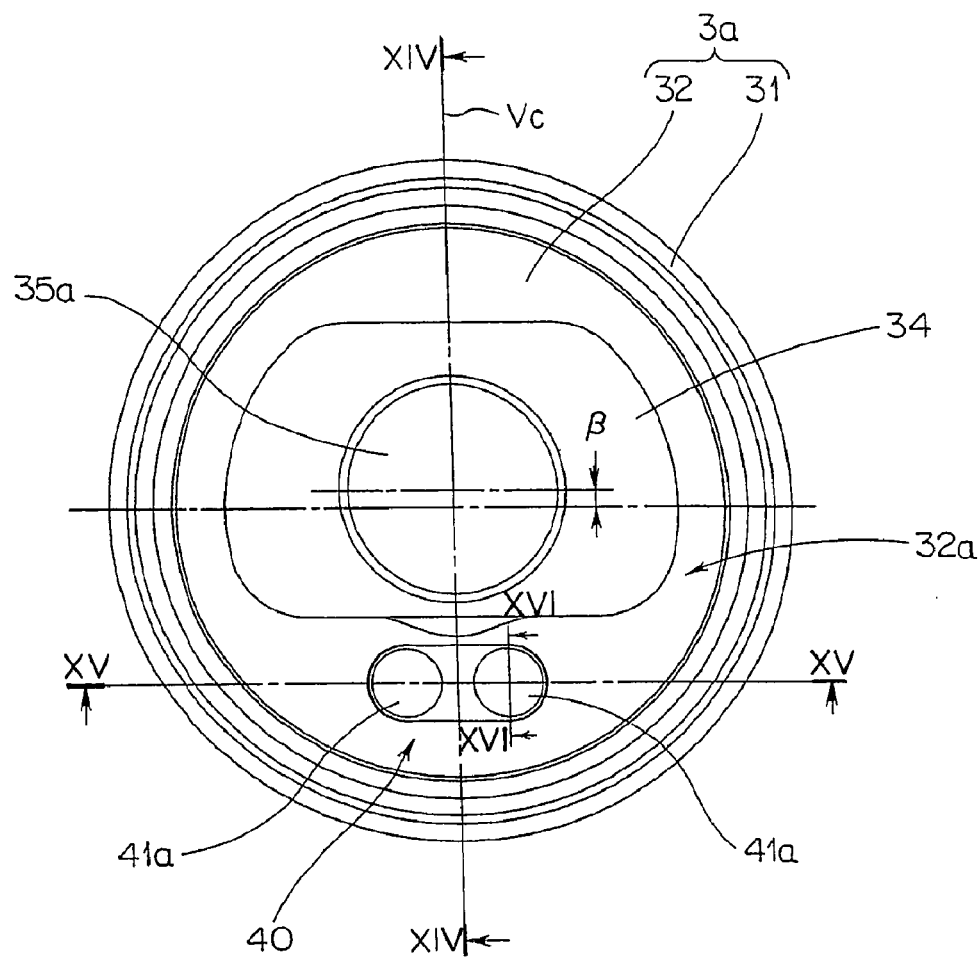
FIG. 13 is a plan view when the insertion portion distal end portion of the endoscope insertion portion is viewed from the front side.
Figure 16:
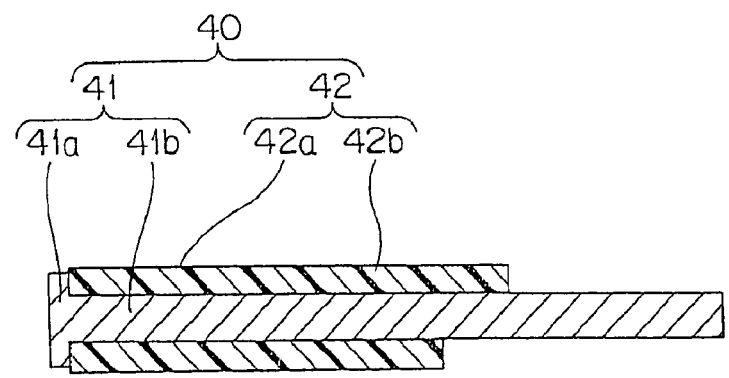
FIG. 16 is a sectional view along the line XVI-XVI in FIG. 13.

As shown in FIG. 13, the distal end portion 3a is configured symmetrically with respect to the vertical axis Vc as the center line in the figure. As described above with reference to FIG. 2, the distal end portion 3a is configured mainly by the exterior portion 31 and the distal end portion main body 32 which is the apparatus main body. The rotation stopping portion 34, and the contact surface portion 41a of the terminal member 41 which configures the endoscope side connection portion 40, are provided so as to project on the distal end side of the distal end portion main body 32. The rotation stopping portion 34 is configured so as to be inserted and arranged in the positioning hole 11d. Also, the distal end adapter 10 and the distal end portion 3a are set in a predetermined positional relationship by arranging the substantially D-shaped rotation stopping portion 34 in the substantially D-shaped positioning hole 11d.

Figure 14:
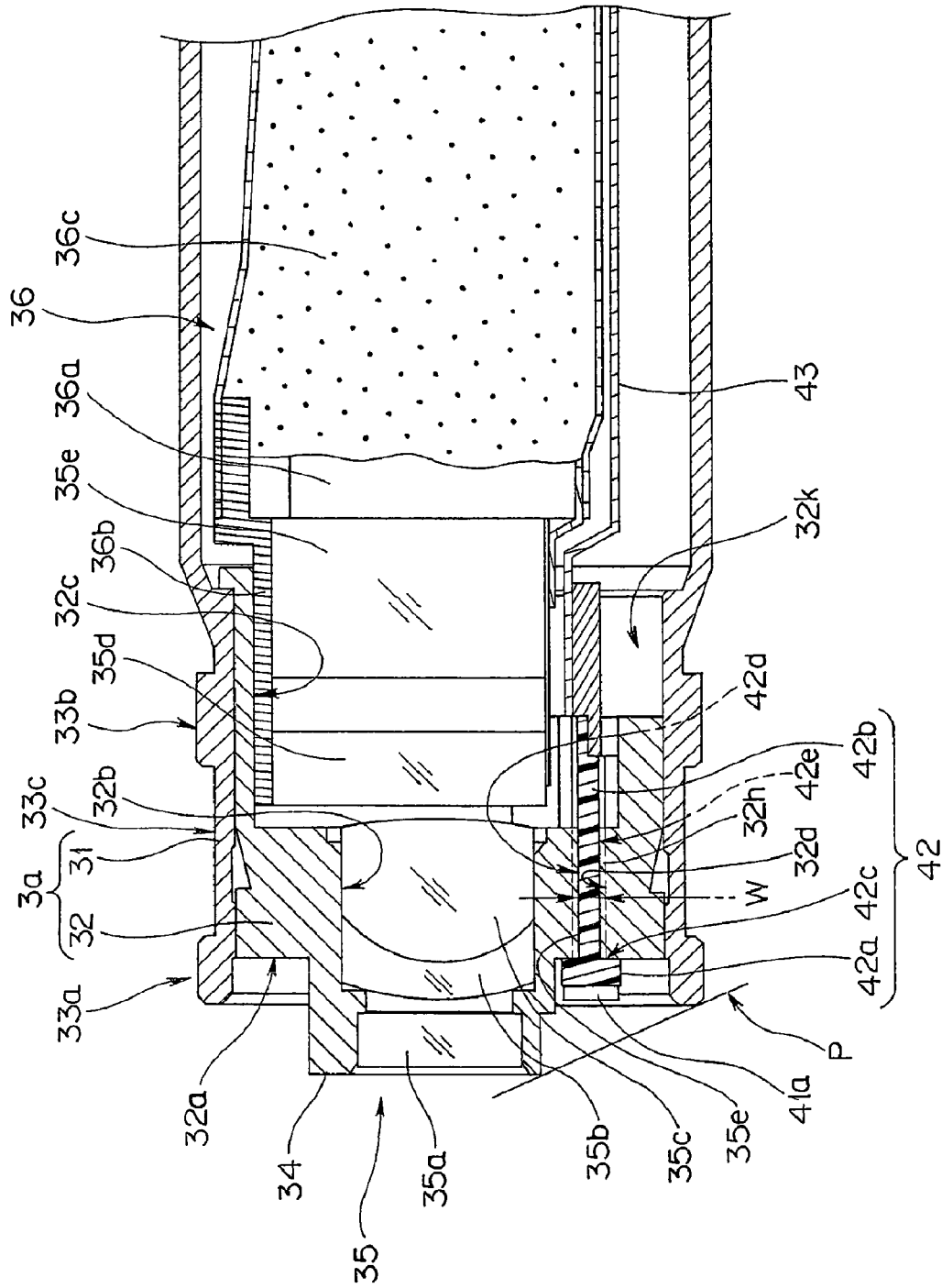
FIG. 14 is a sectional view along the line XIV-XIV in FIG. 13.
Figure 15:
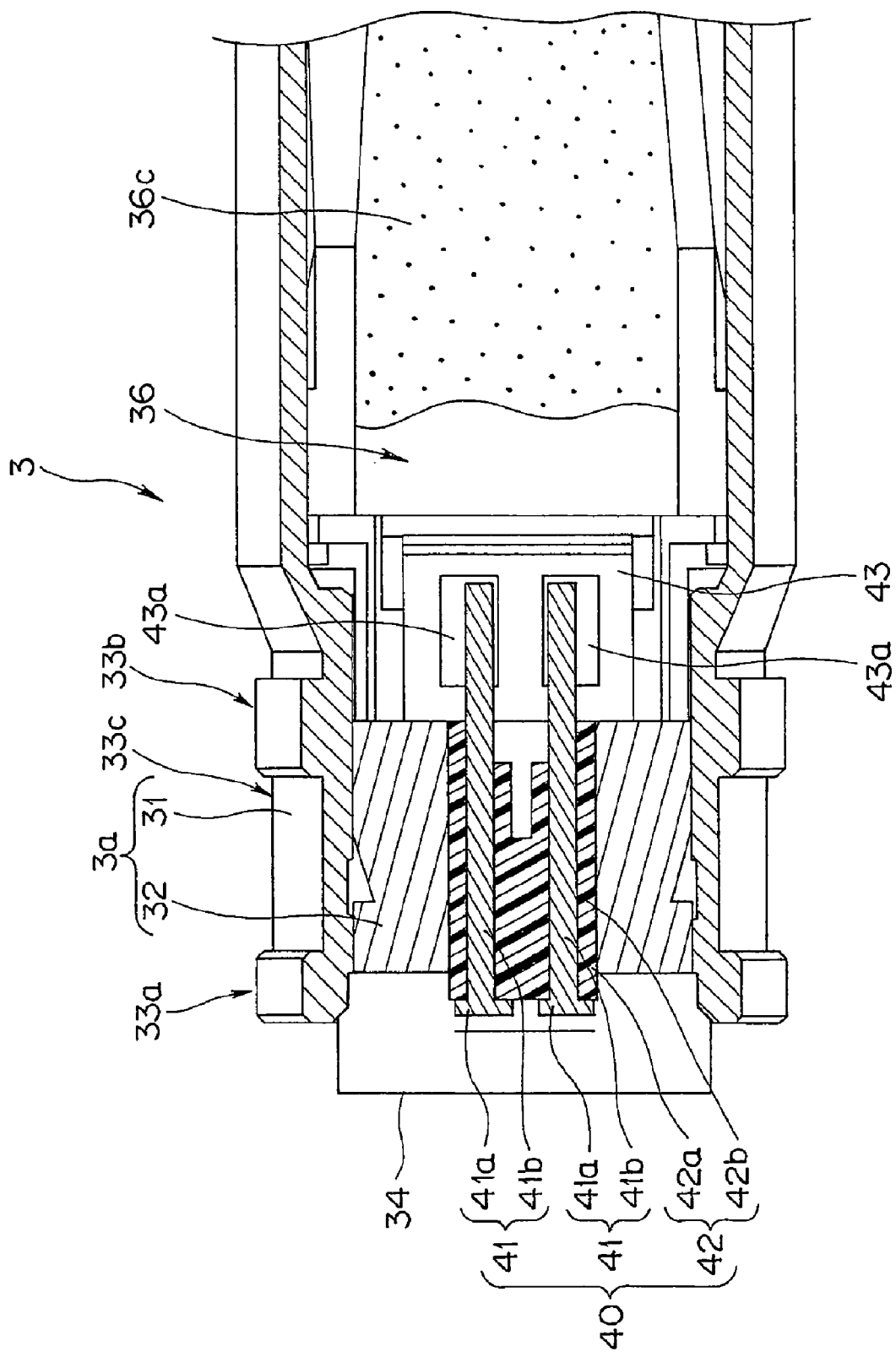
FIG. 15 is a sectional view along the line XV-XV in FIG. 13.

As shown in FIG. 14, in the distal end portion main body 32 which configures the distal end portion 3a, there are provided the distal end lens cover 35a, a stepped lens hole 32b, and an image-pickup hole 32c, which configure the image-forming optical system 35. The stepped lens hole 32b is a hole for arranging a plurality of optical lenses 35b and 35c, and the image-pickup hole 32c is a hole for arranging an image pickup apparatus 36 provided with an image pickup device 36a, such as a CCD. That is, a stepped through hole configured by the image-pickup hole 32c and the stepped lens hole 32b, which have different diameters, is formed in the distal end portion main body 32. An image-pickup frame 36b configuring the image pickup apparatus 36 is arranged in the image-pickup hole 32c. The image-pickup frame 36b is a stepped tubular member having a substantially uniform thickness. In the present embodiment, the distal end part of the image-pickup frame 36b is arranged in the image-pickup hole 32c. A lens cover 35d is arranged on the distal end side of the image-pickup frame 36b, and a cover glass 35e is arranged on the proximal end side of the image-pickup frame 36b. The cover glass 35e is stuck and fixed to a package glass (not shown) provided on the image pickup surface side of the image pickup device 36a.

An image pickup circuit substrate (not shown) is electrically and mechanically connected to the proximal end side of the image pickup device 36a. Electronic components, such as a capacitor and a transistor, are mounted on the image pickup circuit substrate. A signal line which is inserted in the signal cable (not shown) is electrically connected to the image pickup circuit substrate in a predetermined state. The image pickup device 36a, the image pickup circuit substrate, and the like, are sealed by, for example, a thermoplastic resin 36c.

As shown in FIG. 13, FIG. 14, and FIG. 17, an endoscope side connection portion arrangement hole (hereinafter described as second connection portion hole) 32d is formed in the lower part of the distal end portion main body 32 configuring the distal end portion 3a in the figure. The endoscope side connection portion 40 is fixed in the second connection portion hole 32d. The opening shape of the second connection portion hole 32d is a figure-of-8 shape which is substantially the same as the opening shape of the first connection portion hole 11e. Also, the second connection portion hole 32d has the same configuration as that in the first connection portion hole 11e. That is, a first projecting portion 32e provided with a distal end side end surface 32g, and a second projecting portion 32f provided with a distal end side end surface 32h, are formed in parallel to the longitudinal axis direction.

The endoscope side connection portion 40 shown in FIGS. 13 to 17 is configured by the pair of terminal members 41, and an endoscope side insulating portion 42 which configures an exterior sheath. The terminal member 41 is configured by including the disk-shaped contact surface portion 41a and a thin and long rod portion 41b. The contact portion 22c of the second pin member 22 which configures the adapter side connection portion 20 is brought into contact with the disk shaped surface of the contact surface portion 41a. Therefore, the outer diameter of the contact surface portion 41a is configured to be larger than the outer diameter of the rod portion 41b, within a possible range in consideration of the contact state with the contact portion 22c. Note that the terminal member 41 is a conductive member, which is formed of aluminum, brass, iron, or the like, and the surface of the terminal member 41 is plated with a highly conductive material, such as for example, gold.

The endoscope side insulating portion 42 covers the entire periphery of the pair of terminal members 41 in an insulated state by leaving the proximal end side portion of the rod portion 41b of the pair of terminal members 41. The pair of terminal members 41 covered by the endoscope side insulating portion 42 are arranged in parallel with each other at a predetermined interval. The endoscope side insulating portion 42 is configured by a contact surface portion arrangement portion 42a and a covering portion 42b. The contact surface portion arrangement portion 42a is formed like a pedestal, and covers from the proximal end surface of the contact surface portion 41a to a part of the rod portion 41b. Thus, the remaining portion of the endoscope side insulating portion 42, that is, the portion covering the intermediate portion of the rod portion 41b is the covering portion 42b. Note that in the present embodiment, the proximal end side surface of the contact surface portion 41a is in the state of being placed on the distal end surface of the contact surface portion arrangement portion 42a.

A stepped surface formed in the boundary portion between the contact surface portion arrangement portion 42a and the covering portion 42b is a butting surface 42c serving as a positioning surface. A part of the distal end surface 32a of the distal end portion main body 32 including the distal end side end surfaces 32g and 32h is brought into contact with the butting surface 42c. That is, the external shape of the contact surface portion arrangement portion 42a is formed larger than the external shape of the covering portion 42b.

When the endoscope side insulating portion 42 of the endoscope side connection portion 40 is viewed from the front surface side in the state where the pair of contact surface portions 41a are set to face the front surface, the external shape of the contact surface portion arrangement portion 42a is an elliptic shape, in other words, in an approximate figure-of-0 shape. On the distal end surface of the contact surface portion arrangement portion 42a, the contact surface portions 41a of the two terminal members 41 are arranged so as to be separated from each other at a predetermined distance. The contact surface portion arrangement portion 42a prevents the outer peripheral surface of the contact surface portion 41a from being brought into electrical contact with the rotation stopping portion 34. Therefore, the external shape end surface of the contact surface portion arrangement portion 42a is formed wider, in other words, larger than the outer peripheral surface of the contact surface portion 41a, so as to prevent the outer peripheral surface of the contact surface portion 41a from projecting to the outside from the external shape end surface of the contact surface portion arrangement portion 42a. That is, the contact surface portion 41a is arranged on the contact surface portion arrangement portion 42a in such a manner that any part of the contact surface portion 41a is prevented from being extended to the outside from the elliptic outline of the contact surface portion arrangement portion 42a.

The covering portion 42b includes a first recessed portion 42d and a second recessed portion 42e. For this reason, when the covering portion 42b is viewed from the front surface side in the state where the proximal end surface of the rod portion 41b projecting from the covering portion 42b is set to face the front surface, the external shape of the covering portion 42b is an approximate figure-of-8 shape, which is smaller than the above described elliptic shape.

Note that the endoscope side connection portion 40 is configured in such a way that in the state where the pair of terminal members 41 are arranged in parallel with each other at the predetermined interval, the endoscope side insulating portion 42 is provided so as to make the terminal members 41 covered and insulated from each other. In the present embodiment, specifically, the endoscope side connection portion 40 is formed by insert molding. For this reason, the contact surface portion 41a of the terminal member 41 covered by the endoscope side insulating portion 42 is integrally arranged in a close contact state with the contact surface portion arrangement portion 42a.

Further, in the cross sectional shape shown in FIG. 14, the width dimension W of the covering portion 42b provided in the endoscope side insulating portion 42 which configures the endoscope side connection portion 40, is set smaller than the outer diameter dimension of the contact surface portion 41a of the terminal member 41. Further, the first projecting portion 32e is inserted in the first recessed portion 42d, and the second projecting portion 32f is inserted in the second recessed portion 42e.

That is, the adapter side connection portion 20 is configured in such a way that the endoscope side insulating portion 42 is provided around the pair of terminal members 41 which are arranged in parallel with each other at a predetermined interval. In this configuration, the terminal member 41 is configured by including the disk shaped contact surface portion 41a and the rod portion 41b having a diameter smaller than that of the contact surface portion 41a.

The contact surface portion 41a is formed to have a large diameter in consideration of the contact property with the contact portion 22c provided in the second pin member 22. Also, the contact surface portion 41a is arranged on the pedestal-like wide contact surface portion arrangement portion 42a without protruding from the contact surface portion arrangement portion 42a. Therefore, the contact surface portion 41a is prevented from being brought into contact with the distal end portion main body 32 and the rotation stopping portion 34.

On the other hand, the rod portion 41b is formed to have a small diameter within a range in which the property as the conductive member is maintained. Also, the rod portion 41b is covered by the covering portion 42b and the contact surface portion arrangement portion 42a while leaving a part of the proximal end portion. This prevents the rod portions 41b from being brought into contact with each other, and prevents the rod portion 41b from being brought into contact with the distal end portion main body 32. In addition, the width dimension of the covering portion 42b which covers the rod portion 41b formed to have the small diameter, is made smaller than the outer diameter dimension of the contact surface portion 41a of the terminal member 41. Thereby, the reduction in the diameter of the distal end portion 3a is realized.

In this way, in the endoscope side connection portion 40 which is integrally configured by providing the pair of terminal members 41 each having the contact surface portion 41a and the rod portion 41b, and the endoscope side insulating portion 42, it is possible to obtain the contact surface portion 41a which has a large diameter and effects sure contact with the contact portion 22c of the second pin member 22. It is also possible to reduce the width dimension of the covering portion 42b and it is thereby possible to reduce the diameter of the distal end portion 3a.

The endoscope side connection portion 40 is fixed to the second connection portion hole 32d as shown in FIG. 17. When the endoscope side connection portion 40 is inserted and arranged in the second connection portion hole 32d, the side of the rod portion 41b which is exposed from the endoscope side insulating portion 42 configuring the endoscope side connection portion 40, is inserted from the distal end side opening of the second connection portion hole 32d. At this time, the first projecting portion 32e of the second connection portion hole 32d is inserted into the first recessed portion 42d of the covering portion 42b which configures the endoscope side connection portion 40, and the second projecting portion 32f of the second connection portion hole 32d is inserted into the second recessed portion 42e of the endoscope side connection portion 40.

In this insertion state, the endoscope side connection portion 40 is pushed into the second connection portion hole 32d. Then, after the rod portion 41b is projected from the proximal end side opening, the butting surface 42c is brought into contact with the distal end surface 32a of the distal end portion main body 32, which surface includes the distal end side end surfaces 32g and 32h.

Thereby, the endoscope side connection portion 40 is arranged in the second connection portion hole 32d in a predetermined state. At this time, the rod portion 41b of the terminal member 41 which configures the endoscope side connection portion 40, is arranged in a predetermined position in a terminal member arrangement recessed portion 32k in a predetermined state.

Here, the attachment of the endoscope side connection portion 40 to the distal end portion 3a is described with reference to FIG. 14 and FIG. 17.

When attaching the endoscope side connection portion 40 to the distal end portion 3a, the worker applies an adhesive to the side surface portion of the endoscope side insulating portion 42, which is the side surface of the endoscope side connection portion 40. Then, as described above, the worker inserts the side of the rod portion 41b which is exposed from the endoscope side insulating portion 42 of the endoscope side connection portion 40, from the distal end side opening of the second connection portion hole 32d shown in FIG. 17. At this time, the worker inserts the first projecting portion 32e into the first recessed portion 42d, and inserts the second projecting portion 32f into the second recessed portion 42e. In this insertion state, the worker pushes the endoscope side connection portion 40 into the second connection portion hole 32d. Then, the butting surface 42c is brought into contact with the distal end surface 32a of the distal end portion main body 32, which surface includes the distal end side end surfaces 32g and 32h. At this time, the worker holds the abutting state between the endoscope side connection portion 40 and the distal end surface 32a of the distal end portion main body 32, and makes the adhesive cured, so as to thereby fix the endoscope side connection portion 40 to the distal end portion 3a.

Thereby, the pair of terminal members 41 are fixed in the insulated state to the distal end portion main body 32. In this fixed state, the contact surface portion 41a of the pair of terminal members 41 is aligned so as to project by a predetermined amount from the distal end surface of the distal end portion main body 32 to the distal end side. Further, the proximal end portion of the rod portion 41b of the pair of terminal members 41 is arranged so as to project in the terminal member arrangement recessed portion 32k by a predetermined amount from the bottom surface of the terminal member arrangement recessed portion 32k.

Note that in this arrangement state, the contact surface portion 41a of the terminal member 41 is arranged on the recessed position side inside a virtual plane P which is in contact with the distal end of the rotation stopping portion 34, and with the distal end of the exterior portion 31. In other words, the contact surface portion 41a is not projected outside the virtual plane P. For this reason, even when the distal end portion 3a collides with a door, or the like, the contact surface of the door, or the like, collides with the distal end portion 3a as shown by the virtual plane P, and thereby the contact surface portion 41a can be prevented from being damaged.

Further, in this arrangement state, the contact surface portion 41a of the terminal member 41 is arranged in a slightly recessed positional relation to the distal end side surface of the exterior portion 31. This makes it possible to prevent the contact surface portion 41a from being touched carelessly by the worker's finger. Also, even when a foreign matter adheres to the surface of the contact surface portion 41a, or when the surface of the contact surface portion 41a is stained, it is possible to easily clean the surface of the contact surface portion 41a, and to remove the foreign matter.

Further, the pair of rod portions 41b arranged in the terminal member arrangement recessed portion 32k are electrically connected with solder to contact portions 43a which are respectively provided at the other end portions of a flexible substrate 43. An electrical cable extended from the power supply portion not shown is electrically connected to one end portion of the flexible substrate 43.

In this way, the second connection portion hole 32d having the opening shape of the approximate figure-of-8 shape is formed on the distal end surface of the distal end portion main body 32 which configures the distal end portion 3a. On the other hand, the recessed portions 42d and 42e are provided in the covering portion 42b which configures the endoscope side insulating portion 42 configuring the endoscope side connection portion 40. Thereby, the external shape of the covering portion 42b configuring the endoscope side insulating portion 42 becomes the approximate figure-of-8 shape which is coincident with the opening shape of the second connection portion hole 32d. Then, the stepped portion formed by the contact surface portion arrangement portion 42a and the covering portion 42b is used as the butting surface 42c serving as the positioning surface. Thereby, when the figure-of-8 shaped endoscope side insulating portion 42 is inserted and arranged in the figure-of-8 shaped second connection portion hole 32d, the butting surface 42c is brought into contact with the distal end surface of the distal end portion main body 32, which surface includes the distal end side end surface 32g of the first projecting portion 32e and the distal end side end surface 32f of the second projecting portion 32h, which portions are provided in the second connection portion hole 32d.

Thereby, the endoscope side connection portion 40 is positioned and arranged in the predetermined position with respect to the second connection portion hole 32d of the distal end portion 3a. In this contact arrangement state, the endoscope side connection portion 40 is integrally fixed to the distal end portion 3a, so that the insulation of the pair of terminal members can be secured, and the contact surface portion 41a of the pair of terminal members 41 and the pair of rod portions 41b can be arranged in the predetermined positions in the predetermined projecting state.

That is, in the present embodiment, it is possible for the worker to easily perform the work for arranging the two terminal members 41 in the predetermined positions and in the predetermined state, by performing the work for fixing the endoscope side connection portion 40 in the second connection portion hole 32d.

Note that in the above described explanation, it is assumed that the adhesive is applied beforehand to the side surface portion of the endoscope side insulating portion 42 which configures the endoscope side connection portion 40. However, it may also be configured such that after the endoscope side connection portion 40 is arranged in the second connection portion hole 32d in the predetermined state, an adhesive having excellent fluidity is poured into the gap between the endoscope side connection portion 40 and the second connection portion hole 32d, so as to make the endoscope side connection portion 40 stuck and fixed to the second connection portion hole 32d.

Figure 18:
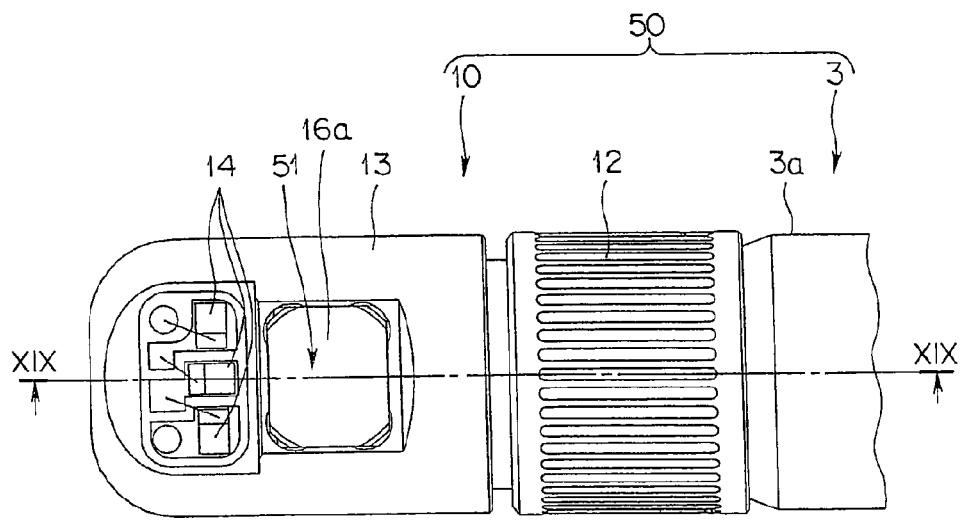
FIG. 18 is a plan view when the adapter type endoscope in the state where the side view type distal end adapter is attached to the insertion portion distal end portion, is viewed from the one surface side of the distal end adapter.

Here, the assembling of the distal end adapter 10 to the distal end portion 3a by the user is described with reference to FIG. 18 and FIG. 19.

When assembling the distal end adapter 10 to the distal end portion 3a, the user first performs positioning of the female screw portion 12a formed in the end portion of the detachable ring 12 and the first male screw portion 33a formed in the exterior portion 31 so that the screw portions are screwed with each other. Then, the user rotates the detachable ring 12 in a predetermined direction, so as to make the female screw portion 12a screwed to the first male screw portion 33a. Thereafter, in this screwed state, the user further rotates the detachable ring 12 in the predetermined direction. Then, the female screw portion 12a is moved beyond the first male screw portion 33a, so that the female screw portion 12a is arranged on the sliding portion 33c so as to be moved back and forth in the axis direction.

Next, the user aligns the positioning hole 11d provided in the adapter main body 11 with the rotation stopping portion 34 provided in the distal end portion main body 32. Then, the user performs a hand operation so as to reduce the relative distance between the detachable ring 12 and the second male screw portion 33b. Then, the rotation stopping portion 34 is inserted in the positioning hole 11d. In this insertion arrangement state, the user performs a hand operation to further reduce the relative distance between the detachable ring 12 and the second male screw portion 33b. Then, the female screw portion 12a formed in the end portion of the detachable ring 12 is brought into contact with the second male screw portion 33b formed in the exterior portion 31.

Here, the user rotates the detachable ring 12 in the predetermined direction in order to make the male screw portion 33b screwed into the female screw portion 12a. Then, the male screw portion 33b is screwed into the female screw portion 12a according to the rotation of the detachable ring 12. Subsequently, when the user continues to rotate the detachable ring 12, the bottom surface of the positioning hole 11d is brought gradually closer to the distal end surface of the rotation stopping portion 34. Then, the contact portion 22c of the second pin member 22 provided in the adapter main body 11 is brought into contact with the contact surface portion 41a arranged on the distal end surface of the distal end portion main body 32.

At this time, the user continues to rotate the detachable ring 12, and hence the contact portion 22c is moved toward the distal end direction of the distal end adapter 10 against the urging force of the coil spring 24. On the other hand, the distal end portion of the exterior portion 31 is brought into contact with the O ring 29, so that the amount of rotating force of the detachable ring 12 is changed. Thereafter, when the user continues to rotate the detachable ring 12, the bottom surface of the rotation positioning hole 11d is brought into contact with the distal end surface of the rotation stopping portion 34. Thereby, as shown in FIG. 18, the attachment of the distal end adapter 10 to the distal end portion 3a is completed, so that an adapter type endoscope 50 is configured.

When the user turns on a power supply switch on the operation panel 6, the control portion 4 provided to the endoscope main body portion 2 can determine the type of the distal end adapter based on the resistance value of the resistor 7 and drive the power supply and the video processor under the optimal condition.

Figure 19:
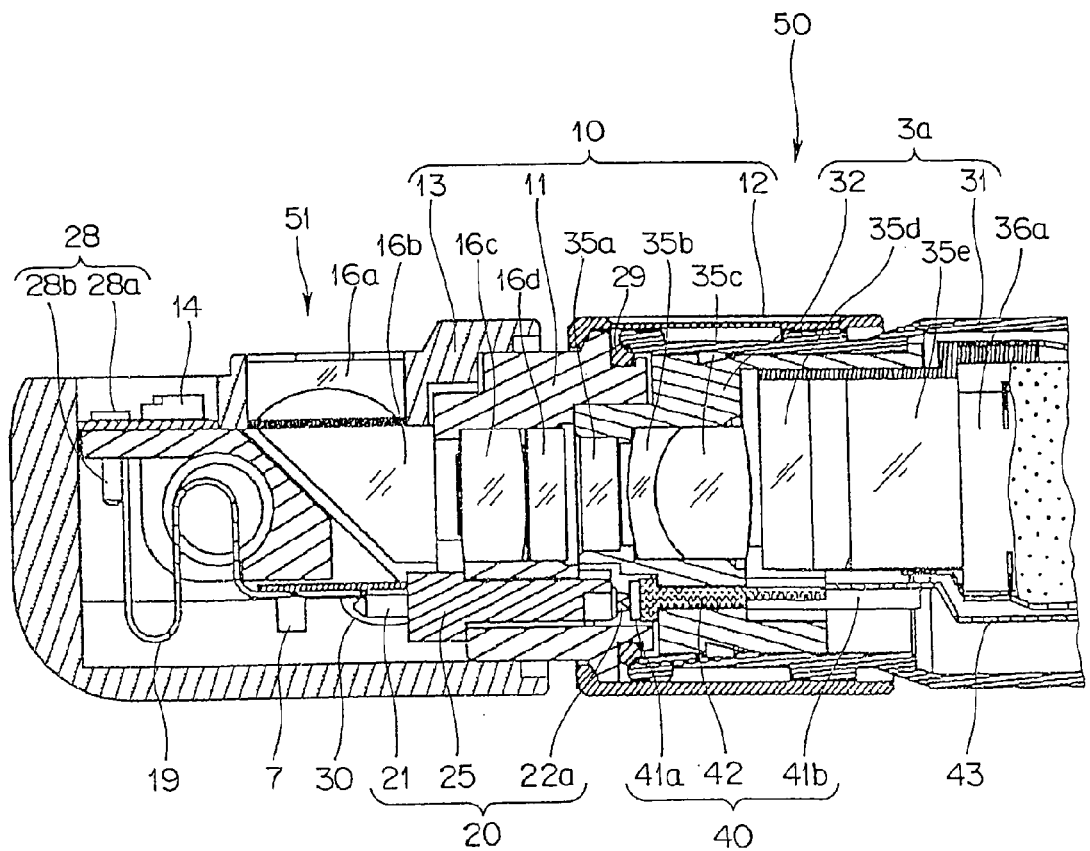
FIG. 19 is a sectional view along the line XIX-XIX in FIG. 18.

In the adapter type endoscope 50 shown in FIG. 19, the contact portions 22c of the second pin members 22 configuring the pair of electrical connection members 26 of the adapter side connection portion 20, is arranged on the contact surface portion 41a of the terminal member 41 configuring the endoscope side connection portion 40 so as to be urged by the urging force of the coil springs 24 configuring the electrical connection member 26. Thereby, the LED 14 mounted on the LED holding plate 18 is electrically connected to the electrical cable extended from the power supply portion via a flexible substrate 43, the terminal member 41 configuring the endoscope side connection portion 40, the second pin member 22 configuring the adapter side connection portion 20, the case body 23, the coil spring 24, the first pin member 21, the flexible substrate 19, the LED electrode 28.

Further, in the adapter type endoscope 50, the distal end lens cover 35a of the image-forming optical system 35 provided in the rotation stopping portion 34 which configures the distal end portion main body 32, is configured to face the second optical lens 16d which is one of the side view optical systems 16 provided in the distal end adapter 10, in a predetermined positional relationship. That is, a side view observation optical system 51 is configured in such a manner that the optical axis of the side view optical system 16 is made coincident with the optical axis of the image-forming optical system 35, and that an optical image passing through the observation window 16a, the prism 16b, the first optical lens 16c, the second optical lens 16d, the distal end lens cover 35a, the optical lens 35b, the optical lens 35c, the lens cover 35d, and the cover glass 35e is formed on the image pickup surface of the image pickup device 36a.

Therefore, in the adapter type endoscope 50, the LED 14 mounted on the LED holding plate 18 is brought into a light-emitting state by supplying electric power to the LED 14 via the electrical cable, so as to illuminate an observation site. On the other hand, the optical image of the observation site illuminated by the LED 14 is formed on the image pickup surface of the image pickup device 36a.

In this way, the contact surface portion 41a of the terminal member 41 provided in the endoscope side connection portion 40 is configured to have a large diameter. Thereby, when the distal end adapter 10 provided with the adapter side connection portion 20 is mounted to the distal end portion 3a provided with the endoscope side connection portion 40, the contact surface portion 41a is surely brought into contact with the contact portion 22c of the second pin member 22 provided in the adapter side connection portion 20, so that an electrical connection state can be obtained.

Further, the second pin member 22 provided in the adapter side connection portion 20 is urged in the projecting direction by the coil spring 24 provided in the adapter side connection portion 20. Therefore, when the distal end adapter 10 provided with the adapter side connection portion 20 is attached to the distal end portion 3a provided with the endoscope side connection portion 40, the electrical connection state can be obtained in such a way that the contact portion 22c of the second pin member 22 provided in the adapter side connection portion 20 is brought into contact with the contact surface arrangement portion 41a of the terminal member 41 in the urged state, that is, the contact portion 22c is pressed against the contact surface arrangement portion 41a by a predetermined pressing force.

Note that the present embodiment assumes that the side view type adapter is used as the distal end adapter 10 of the adapter type endoscope 50. However, the distal end adapter is not limited to the side view type adapter provided with the side view optical system. The distal end adapter may be a direct view type adapter provided with the direct view optical system as the observation optical system as shown in FIGS. 20 to 24, a direct view type adapter for stereoscopic observation (hereinafter referred to as stereo direct view type) as shown in FIGS. 25 to 28, and a stereo direct view type adapter including a channel hole as shown in FIG. 29 to 32.

As shown in FIGS. 20 to 24, a direct view type distal end adapter 10A attachable to the distal end portion 3a is configured by mainly including the adapter main body 11A, the detachable ring 12, and the hood portion 13A. An illumination hole 61 and an optical portion hole 62 are provided in the hood portion 13A. The illumination hole 61 has a substantially cylindrical shape, and the plurality of LEDs 14 are faced from the distal end surface of the illumination hole 61. An observation window 71, and the like, which configures a direct view optical system 70 is arranged in the optical portion hole 62.

Figure 20:
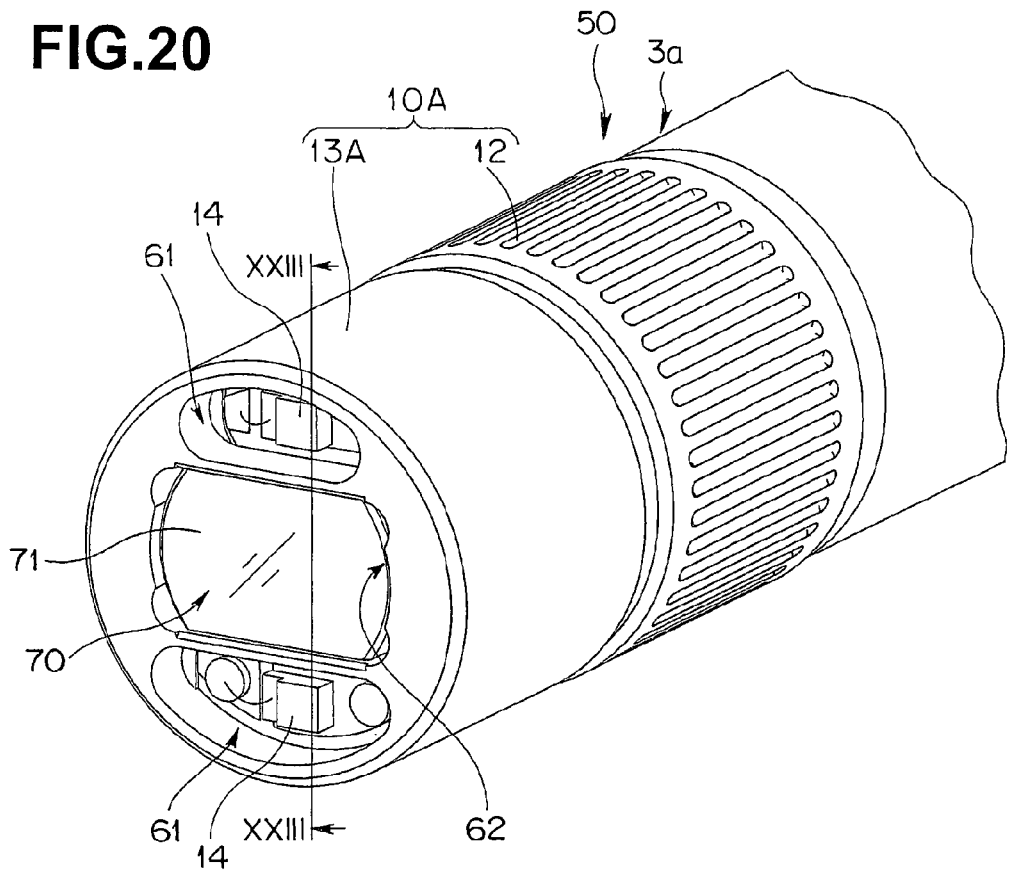
FIG. 20 is a perspective view when the adapter type endoscope in the state where a direct view type distal end adapter is attached to the insertion portion distal end portion, is viewed from the front side of the distal end adapter.
Figure 21:
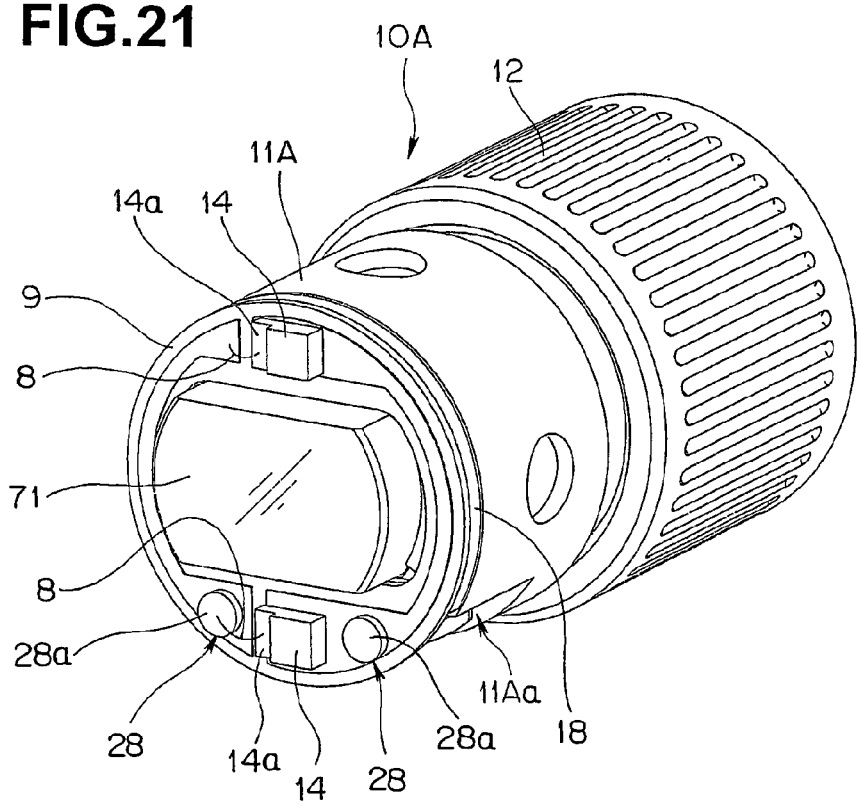
FIG. 21 is a perspective view when the direct view type distal end adapter in the state where the hood portion is removed, is viewed from the front side.
Figure 23:
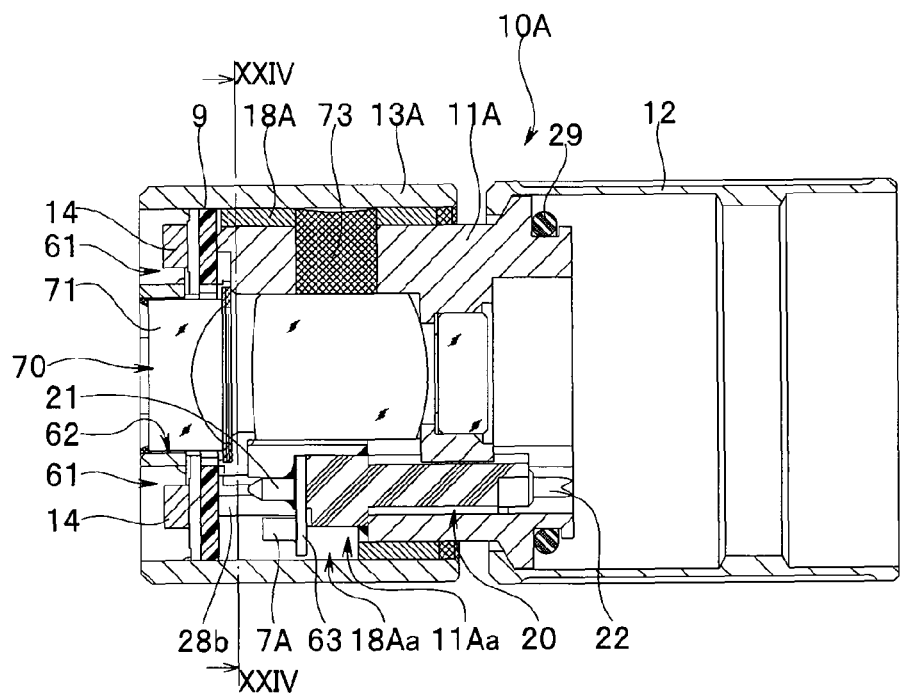
FIG. 23 is a sectional view along the line XXIII-XXIII in FIG. 20.

As shown in FIG. 20, FIG. 21, and FIG. 23, in the direct view type distal end adapter 10A, the LEDs 14 are arranged in an opposing positional relationship so as to sandwich the observation window 71. Further, the pair of LED electrodes 28 are arranged on the side of one of the LEDs 14, which is positioned on the lower side in the figure. The LEDs 14 and the LED electrodes 28 are provided on the substrate 9 fixed to the LED holding plate 18A. The LED holding plate 18A is arranged integrally on the distal end surface of the adapter main body 11A. A pattern 9b is formed beforehand on the substrate 9. The pair of LEDs 14 and the pair of LED electrodes 28 are provided at predetermined positions of the pattern 9b. The contact portion 14a of the LED 14 and the head portion 28a of the LED electrode 28, which are provided on the substrate 9, are electrically connected to each other by the wiring member 8. Further, the pattern 9b and the contact portion 14a of the LED 14 are electrically connected to each other by the wiring member 8.

Figure 22:
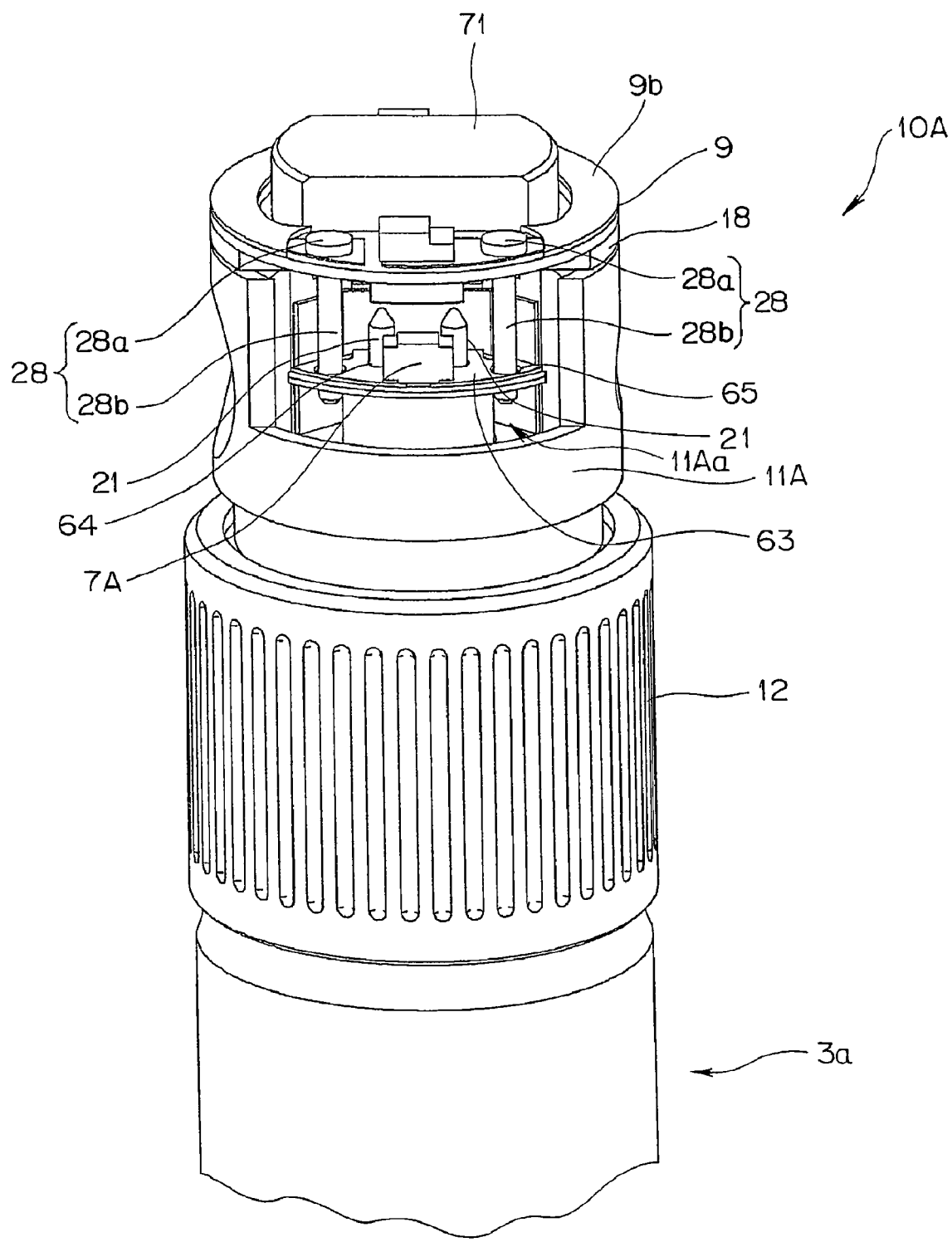
FIG. 22 is a perspective view explaining a positional relationship and an electrical connection between a first pin member and an LED electrode, when the direct view type distal end adapter in the state where the hood portion is removed, is viewed from the side surface side.
Figure 24:
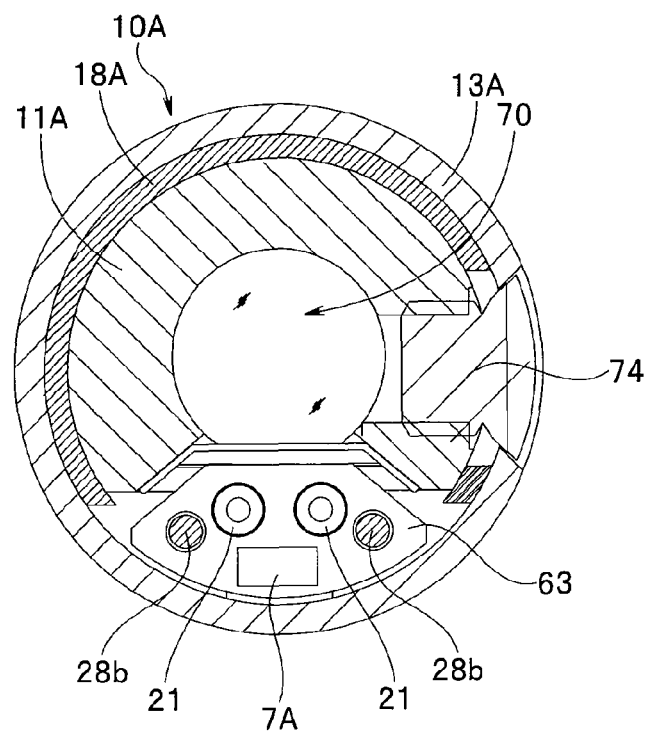
FIG. 24 is a sectional view along the line XXIV-XXIV in FIG. 23.

Also in the direct view type distal end adapter 10A, as shown in FIG. 22 and FIG. 24, the interval between the pair of LED electrodes 28 is different from the interval of the pair of first pin members 21 of the adapter side connection portion 20. For this reason, the electrical connection between the LED electrode 28 and the first pin member 21 is effected, for example, by a substantially fan-shaped rigid substrate 63, for the purpose of pitch adjustment. The fan-shaped substrate 63 includes, on the inner circular arc side, first contact pins 64 corresponding to the first pin members 21, and includes, on the outer circular arc side, second contact pins 65 corresponding to the LED electrodes 28. That is, also in the fan-shaped substrate 63, the pair of first pin members 21 are electrically connected similarly to the flexible substrate 19. The interval between the first contact pins 64 is configured to be smaller than the interval between the second contact pins 65 to which the pin portions 28b are electrically connected.

Further, a resistor 7A for determining the type of the distal end adapter is mounted also on the fan-shaped substrate 63. The resistance value of the resistor 7A is different from the resistance value of the resistor 7. The adapter main body 11A includes a cutout 11Aa. The cutout 11Aa is formed so that the worker can visually recognize the resistor 7A mounted on the fan-shaped substrate 63.

Note that the reference character 73 denotes adhesive. The reference character 18Aa denotes a cutout included in the LED holding plate 18A. In addition, the reference character 74 is a fastening screw with which the hood portion 13A and the adapter main body 11A are integrally fastened.

According to this configuration, the worker can visually recognize the resistor 7A through the cutouts 18Aa and 11Aa. Electric elements may be mounted on the fan-shaped substrate 63.

The fan-shaped substrate is thus provided to the direct view type distal end adapter, and on the fan-shaped substrate is mounted a resistor, a resistance value of which is different from that of the resistor included in the side view type distal end adapter, thereby facilitating the determination of the distal end adapter. In addition, similarly as in the case of the above-described side view type, the configuration of the direct view type adapter makes it possible to prevent accidental contact of the resistor mounted on the fan-shaped substrate with other electronic components and bad electrical contact of the resistor, and also makes it possible for the worker to visually recognize the resistance value of the resistor at the time of assembly work for integrally fixing the adapter main body to the hood portion.

Configuration and working of a stereo direct view type distal end adapter are described with reference to FIGS. 25 to 28.

When a stereo direct view type distal end adapter 10B of the present embodiment is configured, the LED electrodes 28 and the pair of first pin members 21 of the adapter side connection portion 20 are connected by a flexible substrate 19B similarly as in the side view type distal end adapter.

Here, brief description is made on the configuration of the stereo direct view type distal end adapter 10B which is attachable to the distal end portion 3a.

The distal end adapter 10B is configured by mainly including an adapter main body 11B, the detachable ring 12, and a hood portion 13B. The hood portion 13B is provided with the illumination hole 61 and the optical portion hole 62 which are similar to those provided to the hood portion 13A. A plurality of LEDs 14 face the illumination hole 61, and an observation window 71B and the like, which configure a stereo direct view optical system 70B by including a pupil optical system 75, are arranged in the optical portion hole 62.

Also in the distal end adapter 10B, the LEDs 14 are arranged in an opposing positional relationship so as to sandwich the observation window 71B. A pair of LED electrodes 28 are arranged on the side of one of the LEDs 14, which is positioned on the lower side in FIG. 25.

The LED electrodes 28 and the pair of first pin members 21 of the adapter side connection portion 20 are electrically connected by the flexible substrate 19B. On the flexible substrate 19B is mounted a resistor 7B for determining the type of the distal end adapter. The resistance value of the resistor 7B is different from the resistance values of the resistors 7 and 7A.

The reference character 76 denotes a pupil optical lens frame which also serves as the LED holding plate. Other configurations are the same as those of the distal end adapter 10A. The same components are attached with the same reference characters and the descriptions thereof will be omitted.

The resistor 7B, the resistance value of which is different from those of the resistors 7 and 7A, is thus mounted on the flexible substrate 19B, thereby enabling the same working and effect as those of the above-described distal end adapters 10 and 10A to be obtained.

Note that the distal end adapter is assumed to be the stereo direct view type in the present embodiment. However, the distal end adapter is not limited to the stereo direct view type, and the present configuration may be adopted in the stereo side view type distal end adapter.

Figure 25:
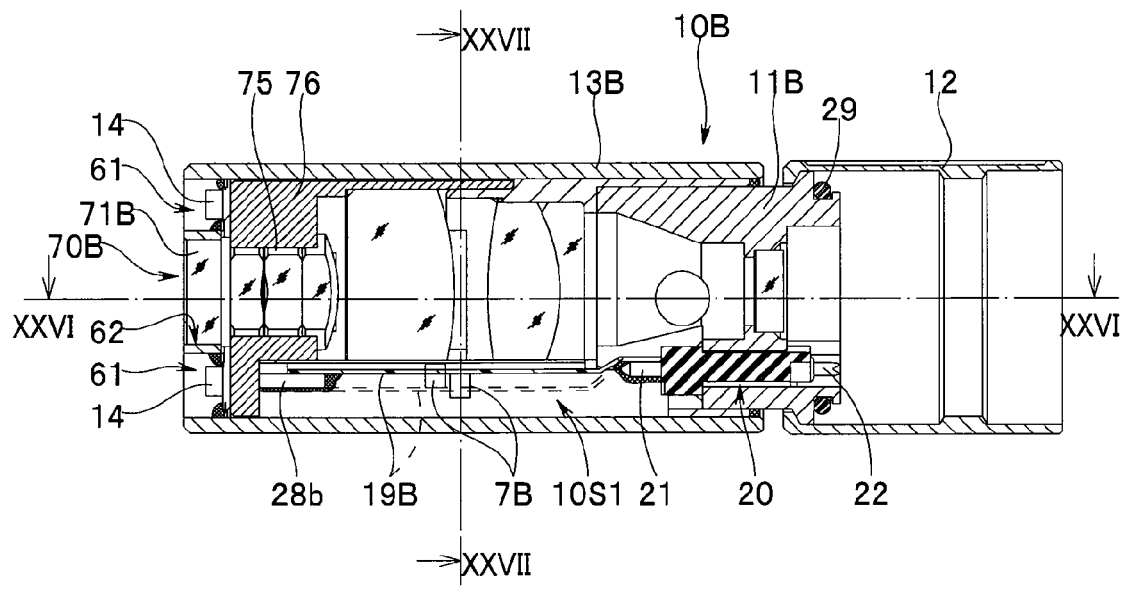
FIG. 25 is a longitudinal sectional view of a stereo direct view type distal end adapter.
Figure 26:
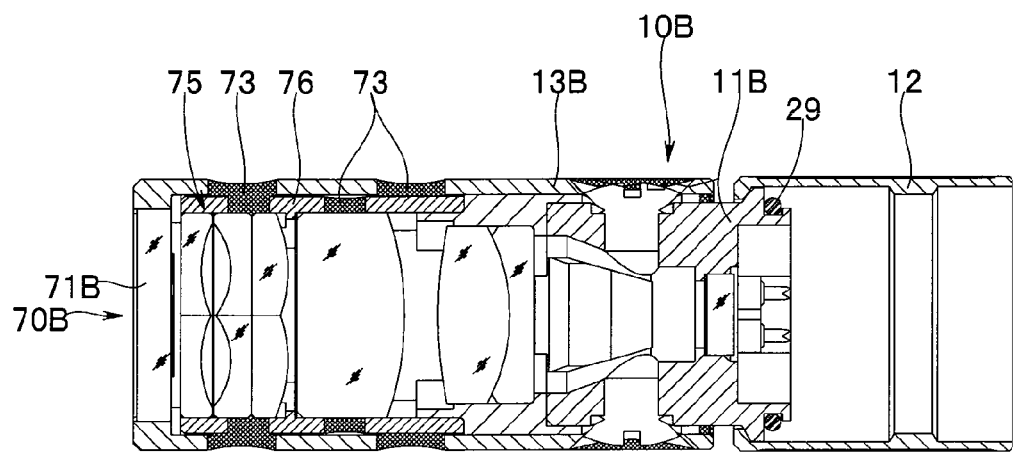
FIG. 26 is a sectional view along the line XXVI-XXVI in FIG. 25.
Figure 27:
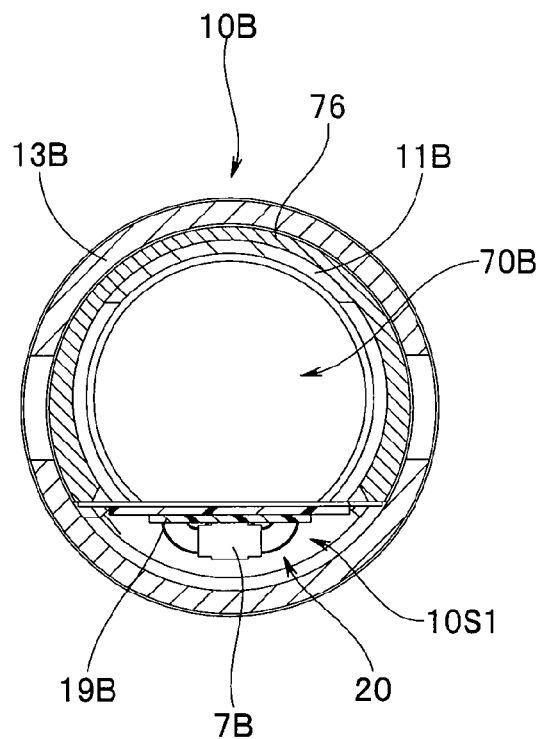
FIG. 27 is a sectional view along the line XXVII-XXVII in FIG. 25.
Figure 28:
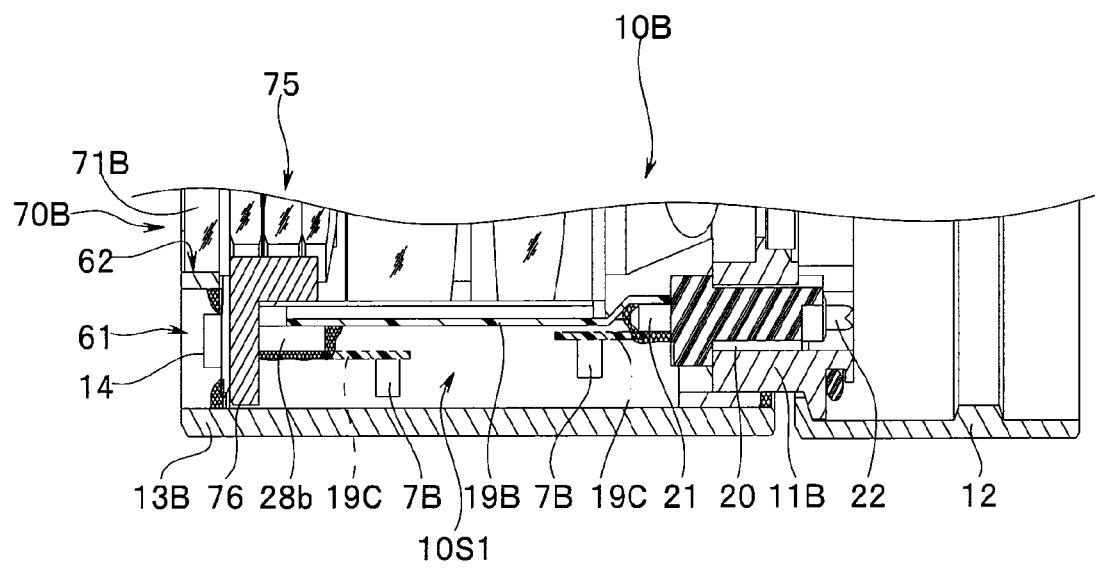
FIG. 28 is a view showing another arrangement example of a resistor for determination.

In addition, as shown by the dashed lines in FIG. 25, the resistor 7B may be mounted on the flexible substrate 19B so as to be positioned not on the side of the hood portion 13B but on the side of the stereo direct view optical system 70B. This configuration enables the worker to visually recognize the resistance value of the resistor 7B from a gap between the flexible substrate 19B and the pupil optical lens frame 76.

Furthermore, the present embodiment assumes that the resistor 7B is mounted on the flexible substrate 19B which electrically connects the LED electrodes 28 and the first pin members 21. However, as shown by the two-dot chain lines or the dashed lines in FIG. 28, the resistor 7B may be mounted on a flexible substrate 19C, for example, which is a member different from the flexible substrate 19B, and the flexible substrate 19C on which the resistor 7B is mounted may be connected to the LED electrodes 28b or to the first pin members 21 as shown in the drawing. Alternatively, the flexible substrate 19C may be connected to the substrate 9, though the illustration thereof is omitted.

Configuration and working of the stereo direct view type distal end adapter including a channel hole are described with reference to FIGS. 29 to 32.

Figure 29:
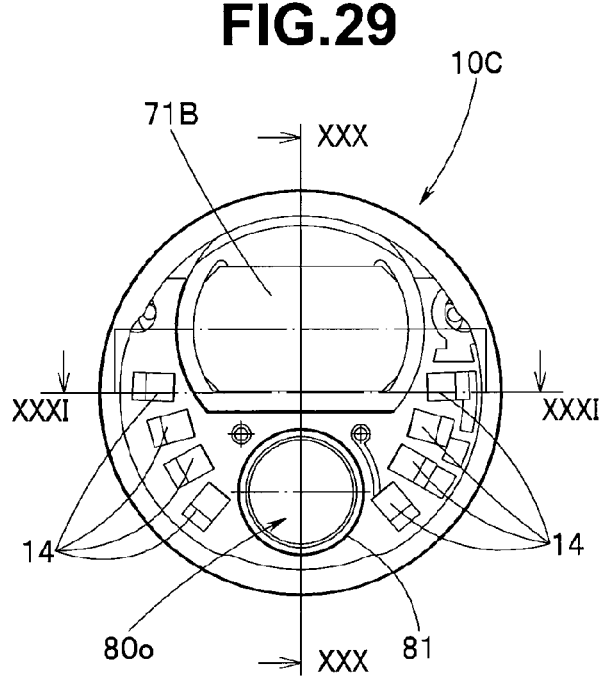
FIG. 29 is a front view of a stereo direct view type distal end adapter including a channel hole.
Figure 30:
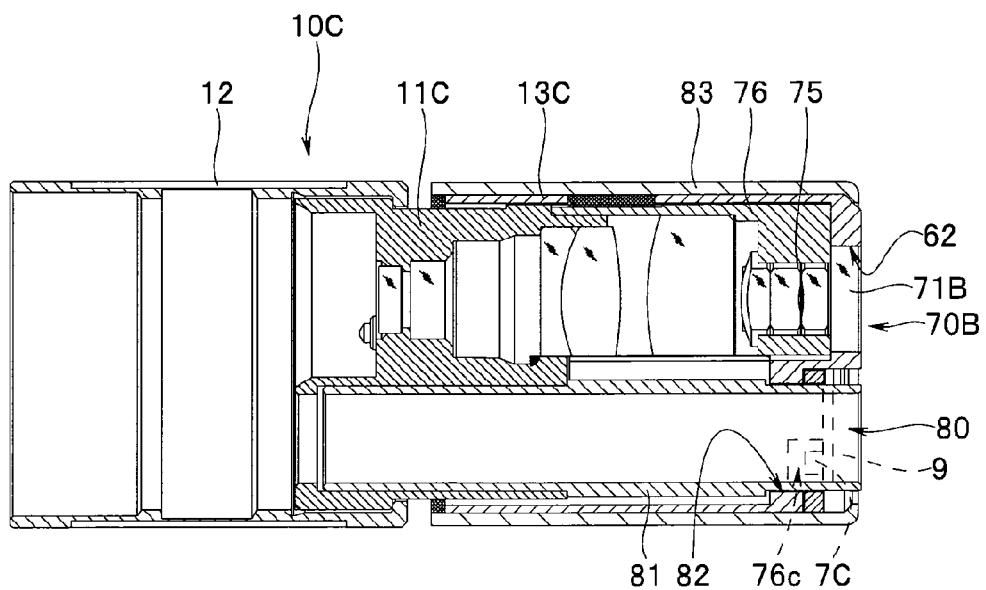
FIG. 30 is a sectional view along the line XXX-XXX in FIG. 29.

If the distal end adapter 10C is the stereo direct view type including a channel hole, a tubular member 81 configuring a channel hole 80 is arranged in an adapter main body 11C, as shown in FIGS. 29 and 30. Therefore, unlike in the case of the adapter 10 and the like, it is difficult to provide the D-shape space 10S1 or the distal end side space 10S2 in the distal end adapter 10C of the present embodiment.

Here, brief description is made on the configuration of the stereo direct view type distal end adapter 10C which is attachable to the distal end portion 3a.

Figure 31:
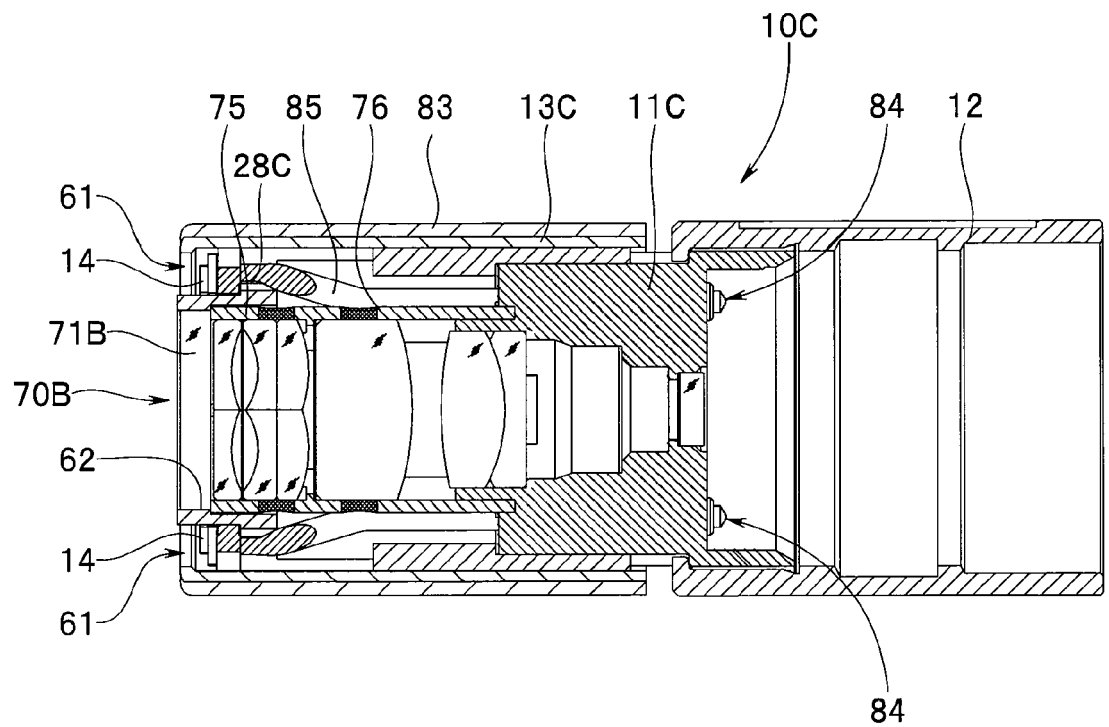
FIG. 31 is a sectional view along the line XXXI-XXXI in FIG. 29.

The distal end adapter 10C is configured by mainly including the adapter main body 11C, the detachable ring 12, and a hood portion 13C. As shown in FIGS. 30 and 31, the hood portion 13C is provided with a tubular member arranging hole 82 in addition to the illumination hole 61 and the optical portion hole 62 which are substantially the same as those provided to the above-described hood portion 13B.

In the tubular member arranging hole 82 is provided the tubular member 81 for configuring the channel hole 80. In addition, a plurality of LEDs 14 face the illumination hole 61 and an observation window 71B and the like, which configure the stereo direct view optical system 70B by including the pupil optical system 75, are arranged in the optical portion hole 62. The reference character 83 denotes a hood portion covering member which is provided on an outer periphery of the hood portion 13B.

Figure 32:
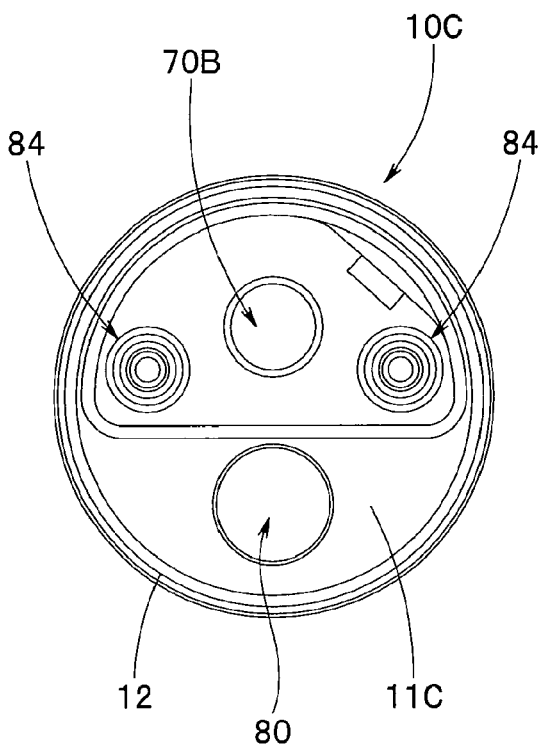
FIG. 32 is a rear view of the stereo direct view type distal end adapter including a channel hole.

In the distal end adapter 10C, the plurality of LEDs 14 are arranged in an opposing positional relationship so as to sandwich the observation window 71B and an opening 80*o* of the channel hole 80 as shown in FIG. 29, and an adapter side connection portion 84 is arranged as shown in FIG. 32. In the present embodiment, an end portion of an electrical cable 85 electrically connected to the adapter side connection portion 84 and extended therefrom is electrically connected to the LED electrodes 28C respectively provided so as to sandwich the observation window 71B and the channel hole 77, as shown in FIG. 31.

As shown by the dashed lines in FIG. 30, a cutout hole 76*c* is formed on the distal end side of the pupil optical lens frame 76. The cutout hole 76*c* is formed in a shape having openings on the distal end side and on the outer peripheral side, and is a space for arranging the resistor 7C for determining the type of the distal end adapter. The resistor 7C is mounted on a surface of the substrate 9, which is opposite side of the surface on which the LEDs 14 are mounted. The resistance value of the resistor 7C is different from the resistance values of the above-described resistors 7, 7A, and 7B.

Other configurations are the same as those of the distal end adapter 10B. The same components are attached with the same reference characters, and the descriptions thereof will be omitted.

The resistor 7C, the resistance value of which is different from those of the resistors 7, 7A, and 7B, is thus mounted on the substrate 9, thereby facilitating the determination of the distal end adapter same as in the cases of the distal end adapters 10, 10A, and 10B.

In addition, the space for arranging the resistor 7C is formed as the cutout hole formed in the shape having openings on the distal end side and the outer peripheral side, thereby enabling the worker to visually recognize the resistor positioned in the space from the opening on the outer peripheral side.

Note that the present embodiment assumes that the distal end adapter is the stereo direct view type including a channel hole. However, the distal end adapter is not limited to the stereo direct view type including a channel hole, and the present configuration may be adopted in the stereo side view type distal end adapter including a channel hole. Alternatively, the present configuration may be adopted in distal end adapters in which it is difficult to provide the D-shape space 10S1 and the distal end side space 10S2.

Figure 33:
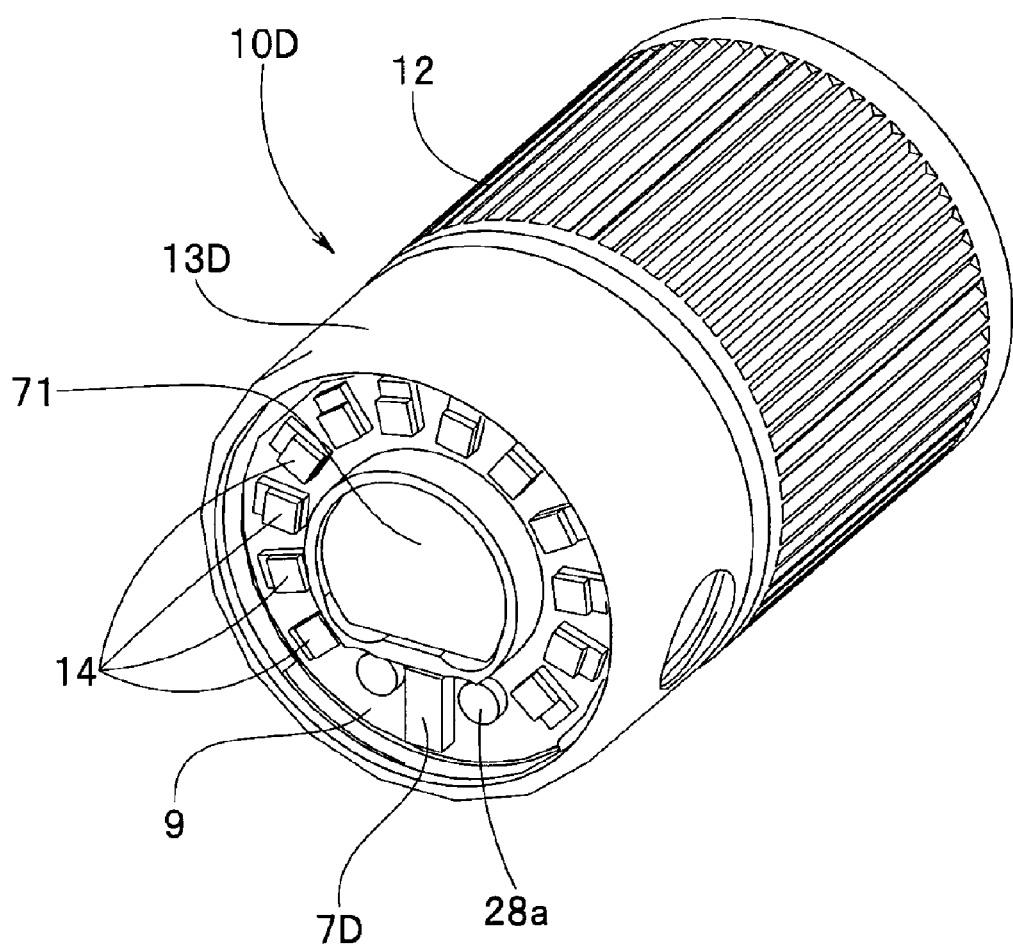
FIG. 33 is a perspective view explaining a distal end adapter having a resistor for determination arranged on a substrate on which a plurality of LEDs are arranged.

Furthermore, as shown in FIG. 33, if there is a space on the substrate 9 on which the plurality of LEDs 14 are arranged around the observation window 71, an adapter 10D may be configured by mounting a resistor 7D, the resistance value of which is different from those of the resistors 7 to 7C in the space on the mounting surface side of the substrate 9. This enables the same working and the effect as those of the distal end adapter 10C to be obtained. The reference character 13D denotes a hood portion.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope adapter including a light emitting diode comprising:

an adapter side detachable portion configured to be attached to an adapter attaching portion provided on a distal end portion of an insertion portion of an endoscope, the insertion portion including, inside the distal end portion thereof, at least one image-forming optical system;

an adapter main body having a connection portion hole and holding an adapter side observation optical system whose optical axis is coincident with an optical axis of the image-forming optical system inside the distal end portion of the insertion portion;

an exterior member having a cylindrical shape in which the adapter main body is disposed and having an opening on a proximal end side thereof on which the adapter side detachable portion is arranged;

a contact pin unit fixed in the connection portion hole of the adapter main body, the contact pin unit comprising an adapter side insulating portion and an electrical connection member which includes a coil spring, a contact pin and a case body;

the case body being a conductive member having a pipe shape, and provided with a caulked portion at an entire periphery of an end portion of the case body for preventing the contact pin from falling off so that the coil spring and the contact pin are retained and configured to be slidable inside the case body;

the coil spring being a conductive member and configured for urging the contact pin slidably arranged in the case body, the contact pin being a conductive member which has a flange portion slidably movable in the case body and brought into contact with the caulked portion by being urged by the coil spring in an axial direction, and has a contact portion configured to be brought into contact with a surface of a contact surface portion of a terminal member included in an endoscope side connection portion provided at the distal end portion of the insertion portion, the adapter side insulating portion integrally covering a pair of the electrical connection portions to be parallel and insulated from each other, a flat connection flexible substrate provided between a substrate on which the light emitting diode is mounted and the contact pin unit, the flat connection flexible substrate being provided with first contact portions configured for electrical connection with a pair of the electrical connection members and second contact portions for electrical connection with the substrate on which the light emitting diode is mounted, the flat connection flexible substrate having a width larger than an interval of the pair of the electrical connection members; and a determination resistor arranged in a space formed in the endoscope adapter and configured to determine a type of the endoscope adapter, wherein a part of the contact pin unit and the flat connection flexible substrate are arranged in a D-shaped space formed by an inner peripheral surface of the exterior member and a plane defining an outer profile of the adapter side observation optical system which is disposed in an optical hole of the adapter main body, so that power supply to the light emitting diode is enabled to be turned on through the contact pin unit fixed in the connection portion hole of the adapter main body when the adapter side detachable portion is attached to the adapter attaching portion.

2. The endoscope adapter according to claim 1, wherein the space in which the determination resistor is arranged is provided between the substrate on which the light emitting diode is mounted and the contact pin unit.

3. The endoscope adapter according to claim 2, wherein the determination resistor is mounted on a substrate electrically connecting the substrate on which the light emitting diode is mounted and the contact pin unit.

4. The endoscope adapter according to claim 3, wherein the substrate is a flexible substrate.

5. The endoscope adapter according to claim 3, wherein the substrate is a rigid substrate.

6. The endoscope adapter according to claim 2, wherein the determination resistor is mounted on another substrate different from the substrate on which the light emitting diode is mounted, and the another substrate on which the determination resistor is mounted is connected to the contact pin unit.

7. The endoscope adapter according to claim 2, wherein the determination resistor is mounted on another substrate different from the substrate on which the light emitting diode is mounted, and the another substrate on which the determination resistor is mounted is connected to the substrate on which the light emitting diode is mounted or to an electrode of the light emitting diode provided on the substrate on which the light emitting diode is mounted.

8. The endoscope adapter according to claim 2, wherein the determination resistor is directly connected to the contact pin unit.

9. The endoscope adapter according to claim 2, wherein the determination resistor is mounted on the substrate on which the light emitting diode is mounted.

10. The endoscope adapter according to claim 9, wherein the determination resistor is mounted on a surface of the substrate, which is an opposite side surface of one surface of the substrate on which the light emitting diode is mounted, and a space, in which the resistor provided on the opposite side surface of the substrate is arranged, is formed on a member configuring the endoscope adapter.

11. The endoscope adapter according to claim 9, wherein the determination resistor is mounted on one surface on which the light emitting diode is mounted.

12. The endoscope adapter according to claim 1, wherein the contact pin is provided to the contact pin unit whose cross-sectional shape is formed in a shape of figure-of-eight.

13. An adapter type endoscope comprising:
an insertion portion extended from an endoscope main body portion, the insertion portion including inside thereof one image-forming optical system and including on a distal end portion thereof an adapter attaching portion; and an endoscope adapter including:
a detachable ring configured to be attached to the adapter attaching portion on the distal end portion;
an adapter main body having a connection portion hole and including an adapter side observation optical system whose optical axis is coincident with an optical axis of the image-forming optical system;
an exterior member having a cylindrical shape in which the adapter main body is disposed and having an opening on a proximal end side thereof on which the adapter side detachable portion is arranged;
a contact pin unit fixed in the connection portion hole of the adapter main body, the contact pin unit comprising an adapter side insulating portion and an electrical connection member which includes, a coil spring, a contact pin and a case body;
the case body being a conductive member having a pipe shape, and provided with a caulked portion at an entire periphery of an end portion of the case body for preventing the contact pin from falling off so that the coil spring and the contact pin are retained and configured to be slidable inside the case body,
the coil spring being a conductive member and configured for urging the contact pin slidably arranged slidably in the case body,
the contact pin being a conductive member which has a flange portion slidably movable in the case body and brought into contact with the caulked portion by being urged by the coil spring in an axial direction, and has a contact portion configured to be brought into contact with a surface of a contact surface portion of a terminal member included in an endoscope side connection portion provided at the distal end portion of the insertion portion,
the adapter side insulating portion integrally covering a pair of the electrical connection portions to be parallel and insulated from each other,
a flat connection flexible substrate provided between a substrate on which a light emitting diode is mounted and the contact pin unit;
first contact portions configured for electrical connection with a pair of the electrical connection members;
second contact portions configured for electrical connection with the substrate on which the light emitting diode is mounted, the flat connection flexible substrate having a width larger than an interval of the pair of the electrical connection members; and
a determination resistor provided for each adapter and configured to determine a type of the adapter,
wherein a part of the contact pin unit and the flat connection flexible substrate are arranged in a D-shaped space formed by an inner peripheral surface of the exterior member and a plane defining an outer profile of the adapter side observation optical system which is disposed in an optical hole of the adapter main body, so that power supply to the light emitting diode is enabled to be turned on through the contact pin unit fixed in the connection portion hole of the adapter main body when the adapter side detachable portion is attached to the adapter attaching portion.

* * * * *